(12) United States Patent
Hogue et al.

(10) Patent No.: US 6,490,532 B1
(45) Date of Patent: Dec. 3, 2002

(54) METHOD TO CONSTRUCT PROTEIN STRUCTURES

(75) Inventors: Christopher Hogue, Oakville; Howard Feldman, Willowdale, both of (CA)

(73) Assignee: Mount Sinai Hospital, Toronto (CA)

( * ) Notice: Subject to any disclaimer, the term of this patent is extended or adjusted under 35 U.S.C. 154(b) by 0 days.

(21) Appl. No.: 09/491,102

(22) Filed: Jan. 25, 2000

Related U.S. Application Data

(60) Provisional application No. 60/117,156, filed on Jan. 25, 1999.

(51) Int. Cl.[7] ............................................... G06F 19/00
(52) U.S. Cl. .............................. 702/27; 702/19; 702/20; 703/2; 703/11
(58) Field of Search .............................. 702/19, 20, 27; 703/2, 11

(56) References Cited

U.S. PATENT DOCUMENTS

| | | | | |
|---|---|---|---|---|
| 5,241,470 A | * | 8/1993 | Lee et al. ............... | 364/413.15 |
| 5,680,319 A | * | 10/1997 | Rose et al. .................. | 364/496 |

OTHER PUBLICATIONS

Bassolino–Klimas et al., "Application of a Directed Conformational Search for Generting 3–D Coordinates for Protein Structures From alpha–Carbon coordinates", PROTEINS: Structure, Function and Genetics (1992) vol. 14 pp. 465–474.*

Monge et al., "Computer Modeling of Protein Folding: Conformational and Energetic Analysis of Reduced and Detailed Protein Models", J. Mol. Biol. vol. 247 (1995) pp. 995–1012.*

Gender et al., "A Molecular Dynamics Approach for the Generation of Cjomplete Protein Structures From Limited coordinate Data", Proteins: Structure, Function, and Genetics (1994) vol. 18 pp. 174–185.*

Boris, J. (1986) J. Comput. Phys., 66, 1–20.

Lambrakos, S.G., and Boris, J.P. (1987) J. Comput. Phys., 73, 183–202.

Ambrosiano, J., Greengard, L., and Rokhlin, V. (1988) Computer Physics Communications, 48, 117–125.

Appel, A.W., (1985) SIAM J. Sci. Stat. Comput., 6, 85–103.

Greengard, L., and Rokhlin, V. (1987) J. Comput. Phys., 73, 325–348.

Omohundro, S.M. (1987) Complex Systems, 1, 273–347.

Van Gunsteren, W.V. Berendsen, H.J.C., Colonna, F., Perahia, P., Hollenberg, J.P., and Lellouch, P. (1984) J., Comput. Chem., 5, 272–279.

Barnes, J. and Hut, P. (1986) Nature, 324, 446–449.

Karfunkel, H.R. and Eyraud, U. (1989) J. Comput. Chem., 10, 628–634.

(List continued on next page.)

Primary Examiner—Mary K. Zeman
(74) Attorney, Agent, or Firm—Merchant & Gould P.C.

(57) ABSTRACT

A computer-implemented method for creating all-atom, real-space protein conformers. The method involves constructing a backbone structure of α-carbons of a protein from the amino acid sequence of the protein by adding and removing carbon atoms through chain elongation and backtracking. An atom is positioned based on a predicted two-dimensional space, and backtracking removes an atom if it is closer to its neighbour than allowed by van der Waals radii. The method also involves positioning β carbons, C, N, and O atoms to provide favourable bond lengths and bond angles, and positioning sidechain rotamers.

13 Claims, 29 Drawing Sheets

(3 of 29 Drawing Sheet(s) Filed in Color)

OTHER PUBLICATIONS

Hernquist, L. (1988) Computer Physics Communications, 48, 107–115.

Katzenelson, J. (1989) Sian J. Sci. Stat. Comput., 10, 787–815.

Lyklema, J.W., (1984) J. Phys A: Math. Gen., 17, L691–L696.

Majid, I., et al., (1984) Phys. Rev. Lett., 52, 1257–1260.

Pietronero, L. (1985) Phys. Rev. Lett., 55, 2025–2027.

de la Cruz, X.F., et al. (1997) Fold. Des., 2:223–234.

Ramachandran, G.N. and Sasisekharan, V. (1968) Adv. Protein Chem., 23:283–438.

Ngo, J.T. and Marks, J. (1992) Protein Eng., 5:313–321.

Karplus, M. (1997) Fold. Des., 2:S69–S75.

Broder, A.J., Pattern Recognition, vol. 23, No.1/2, p. 171, 1990.

Rey, A. and Skolnick,J. (1992) J. Comp. Chem., 13:443–456.

Holm, L. and Sander, C. (1991) J. Mol. Biol., 218:183–194.

Correa, P.E. (1990) Proteins, 7:366–377.

Dunbrack, R.L.J., and Karplus, M. (1993) J. Mol. Biol., 230:543–574.

Brant, D.A. and Flory, P.J. (1965) J. Amer. Chem. Soc., 87:2791–2800.

Hogue, C.W. (1997) Trends. Biochem. Sci., 22:314–316.

Cremer, D. and Pople, J.A. (1975) J. Amer. Chem. Soc. 97:1354–1358.

Lee, C. (1994) J. Mol. Biol., 236:918–939.

Hooft, R.W. et al. (1996) Nature, 381:272.

Lee, C. and Subbiah, S. (1991) J. Mol. Biol., 217:373–388.

Netzer, W.J. and Hartl, F.U. (1998) Trends. Biochem. Sci., 23:68–73.

Netzer, W.J. and Hartl, F.U. (1997) Nature, 388:343–349.

Gregoret, L.M. and Cohen, F.E. (1991) J. Mol. Biol., 219:109–122.

Engh, R.A. and Buher, R. (1991) Acta Cryst., A47:392–400.

Wang, Y. et al. (1998) Fold. Des., 3:1–10.

Kim, B.S. and Park, S. B. (1986) IEEE Transactions on Pattern Analysis and Machine Intelligence, vol. PAMI–8, No. 6, 761–765.

Vohwinkel, C. (1988) Computer Physics Communications, 51:323–330.

Eastman, C.M. and Weiss,S.F. (1982) Inform System, vol. 7 No. 2:115–122.

Onuchic, et al. (1995) Proc. Natl. Acad. Sci, 92:3626–3630.

* cited by examiner

METHOD TO CONSTRUCT PROTEIN STRUCTURES

This application claims priority to U.S. Provisional Application Ser. No. 60/117,156 filed Jan. 25, 1999.

A portion of the disclosure of this patent document contains material which is subject to copyright protection. The copyright owner has no objection to the facsimile reproduction by any one of the patent disclosure, as it appears in the Patent and Trademark files or records, but otherwise reserves all copyright rights whatsoever.

FIELD OF THE INVENTION

The invention relates to a computer-implemented method for determining all-atom, real-space protein structures.

BACKGROUND OF THE INVENTION

Protein sequences can be deduced from the DNA sequence of an organism, and the worldwide genome project has provided tens of thousands of new protein sequences. Proteins have flexible backbones, and protruding, rotating side-chains. They can take up a countless number of shapes i.e. conformations, in three-dimensional space. Yet proteins eventually fold into an ordered structure, the native conformation. The protein-folding problem reflects the inability to predict the native folded conformation of a protein given only its amino acid sequence.

Various methods have been described for solving the folding problem. The methods include direct and template-based methods. Direct methods try to determine the native conformation as a lowest energy point in some defined hyperspace of conformational possibilities. Template-based methods compare a sequence of unknown three-dimensional structure against a library of known three-dimensional structure and score good matches as likely folds. There is a substantive body of research literature on these methods, but successes are rare and often not reproducible. There has been a call for new computational methods that broadly explore comformational space and that are true to the details of protein structure (Dill, K. A. et al Nature Structural Biology 4:10, 1997; Karpus, M. Fold Des. 2:S69, 1997).

SUMMARY OF THE INVENTION

The present inventors have developed a method to generate plausible random protein structures. All-atom proteins are made directly in continuous 3-dimensional space starting from primary sequence with an N to C directed build-up method. The method uses a novel pipelined residue addition approach in which the leading edge of the protein is constructed 3 residues at a time for optimal protein geometry, including the placement of cis proline. Build-up methods represent a classic N-body problem, expected to scale as $N^2$. When proteins become more collapsed, build-up methods are susceptible to backtracking problems which can scale exponentially with the number of residues required to back out of a trapped walk. Solutions to both these problems have been provided, using a multiway binary tree that makes the N-body problem of bump-checking scale as NlogN, and speeding up backtracking by varying the number of tries before backtracking based on available conformational space.

In particular, the method constructs all-atom protein structures in O(NlogN) time (rather than in quadratic $O(N^2)$ time) by residue addition that is balanced in both speed and detail. The primary sequence and a multidimensional trajectory graph system is employed, which directs the sampling of conformational space and behaves like the theoretical protein folding funnel. Trajectory graphs can direct either the random sampling of protein conformer space (the funnel "mouth"), or direct the reconstruction of a known protein backbone (the funnel "spout"). Several novel geometrical, methodological, and algorithmic approaches are introduced in the method. A schematic diagram of a method of the invention is shown in FIG. 1.

The methods of the invention have been validated at both extremes of the folding funnel by comparison with polymer theory, and by reconstructing known proteins. In particular, random all-atom proteins generated using the *E. coli* genomic amino acid composition had radius of gyration statistics that showed the expected swelling compared to non-self avoiding random polyalanine, and Flory's (12) theoretical curves approximate a lower bound for these results. For tests of protein fold reconstruction using nine different protein folds, an average RMSD of 0.63 Å was obtained for Cβ, C, N and O backbone atoms. WHAT_ CHECK, a protein-structure checking software suite (30) validated that the method generates physically and chirally valid backbones and sidechains, The binary-d tree is a new hierarchical data structure developed to deal with the $O(N^2)$ problem of atomic bump-checking (collision detection based on atomic radii). It permits overall O(NlogN) time complexity (validated out to N=2,500 amino acids), together with efficient backtracking. It utilizes a unique 3-dimensional tree that partitions space in a relative fashion unlike voxels used in an octree system. Branch and bound search methods on the binary-d tree can retrieve coordinates contained by probe volumes. The method allows atoms or sections of molecules to be moved without repartitioning the space occupied by the entire set of atoms. Binary searches are also used in the fitting of amino acid backbones between alpha-carbons, and in the random sampling of the trajectory graphs, which also contribute to the overall O(NlogN) performance of the method of the invention.

Therefore, in accordance with an aspect of the invention a method is provided for creating or identifying a conformation of a protein of known or unknown structure which comprises the steps of;

(a) providing an amino acid sequence of the protein;

(b) constructing a backbone structure of α-carbons of the protein by adding and removing carbon atoms through chain elongation and backtracking, wherein an atom is positioned based on a predicted two-dimensional space, and wherein backtracking removes an atom if it is closer to its neighbour than allowed by van der Waals radii;

(c) positioning β carbons, C, N, and O atoms to provide favourable bond lengths and bond angles; and (d) positioning sidechain rotamers; thereby outputting a conformation of the protein.

The method constructs the conformation of the protein in O(NlogN) time, and it is constructed in real space and not confined to a lattice. The conformation is preferably an all atom protein structure, including hydrogen atoms. The method may further comprise assembling different conformations of the protein to provide an ensemble of conformations of the protein. The ensemble may be incorporated in a database which may comprise from about 50,000 to 500,000 different conformations of the protein.

Another aspect of the invention is a computer-implemented process for identifying a conformation of a protein of known or unknown structure from an amino acid sequence of the protein. The steps of the process performed by the computer include (a) constructing a backbone structure of α-carbons of the protein by adding and removing carbon atoms through chain elongation and backtracking, wherein an atom is positioned based on a predicted two-dimensional space, and wherein backtracking removes an atom if it is closer to its neighbour than allowed by van der Waals radii; (b) positioning β carbons, C, N, and O atoms to provide favourable bond lengths and bond angles; and (c) positioning sidechain rotamers; thereby identifying a conformation of the protein.

Another aspect of the invention is part of a computer system for creating or identifying a conformation of a protein of known or unknown structure from an amino acid sequence of the protein. This part of the computer system includes (a) means for constructing a backbone structure of α-carbons of the protein by adding and removing carbon atoms through chain elongation and backtracking, wherein an atom is positioned based on a predicted two-dimensional space, and wherein backtracking removes an atom if it is closer to its neighbour than allowed by van der Waals radii; (b) means for positioning β carbons, C, N, and O atoms to provide favourable bond lengths and bond angles; and (c) means for positioning sidechain rotamers.

Another aspect of the invention is part of a computer system for identifying favorable areas of conformational space in an ensemble of conformations of a protein. This part of the computer system includes a conformer generator module and a structure analysis module. The conformer generator module has an input for receiving an amino acid sequence of the protein and it defines an ensemble of conformations of the protein by (a) constructing a backbone structure of α-carbons of the protein by adding and removing carbon atoms through chain elongation and backtracking, wherein an atom is positioned based on a predicted two-dimensional space, and wherein backtracking removes an atom if it is closer to its neighbour than allowed by van der Waals radii; (b) positioning β carbons, C, N, and O atoms to provide favourable bond lengths and bond angles; and positioning sidechain rotamers. The module records the amino acid sequence of the protein as an ensemble of conformations of the protein wherein each conformer of the protein is represented by a backbone conformation graph. The structure analysis module is connected to the output of the conformer generator module and it comprises means for creating or identifying a next ensemble of conformers of the protein using a weighting scheme and scoring function; and means for repeating these steps until the backbone conformation graph maintains its shape.

Backbone structures of α-carbons of a protein may be constructed by randomly sampling "trajectory graphs" or "trajectory distributions" of amino acid residues representing a statistical sampling for each amino acid residue of the conformational space it is observed to visit in known proteins wherein the trajectory graphs are resolved into α, β, and coil secondary structure components for each amino acid residue. The secondary-structure based trajectory graphs may be recombined in predicted proportions (e.g. %α, %β, % coil) for each amino acid in a protein to be analyzed to form a starting backbone conformation graph. Electron microscopy, atomic microscopy, and/or NMR data may also be used to confine selected conformational spaces i.e. the data may be mapped into the trajectory graphs.

The invention contemplates a part of a computer system for constructing backbone structures of α-carbons of a protein comprising a trajectory file which defines trajectory graphs or distributions of amino acid residues representing a statistical sampling for each amino acid residue of the conformational space it is observed to visit in known proteins wherein the trajectory graphs are resolved into α, β, and coil secondary structure components for each amino acid type; and optionally the graphs are recombined in predicted secondary structure proportions for the protein.

The invention provides a novel hierarchical data structure (i.e. binary-d tree) that fits residues in the backbone structure of a protein between α-carbons and in random sampling of the trajectory graphs.

Another aspect of the invention is a computer-implemented process for identifying favorable conformational spaces in an ensemble of conformations of a protein comprising:

(a) providing a database of conformations of the protein wherein each conformer is represented by a backbone conformation graph;

(b) creating a next ensemble of conformations of the protein using a weighting scheme and scoring function; and (c) repeating step (b) until the backbone conformation graph maintains its shape.

The methods and processes of the invention provide an ensemble of conformations of a protein i.e. conformers. Each protein in an ensemble may be generated using the method of the invention on a single processor. Other advantages of the processes and methods of the invention include fixed memory usage, minimal disk usage, and many adjustable parameters to affect the quality versus speed tradeoff of structure generation.

The details of the preferred embodiment of the present invention are set forth in the accompanying drawings and the description below. Once the details of the invention are known, numerous additional innovations and changes will become obvious to one skilled in the art.

DESCRIPTION OF THE DRAWINGS

The invention will be better understood with reference to the drawings in which.

DETAILED DESCRIPTION OF PREFERRED EMBODIMENTS OF THE INVENTION

Figure 1:
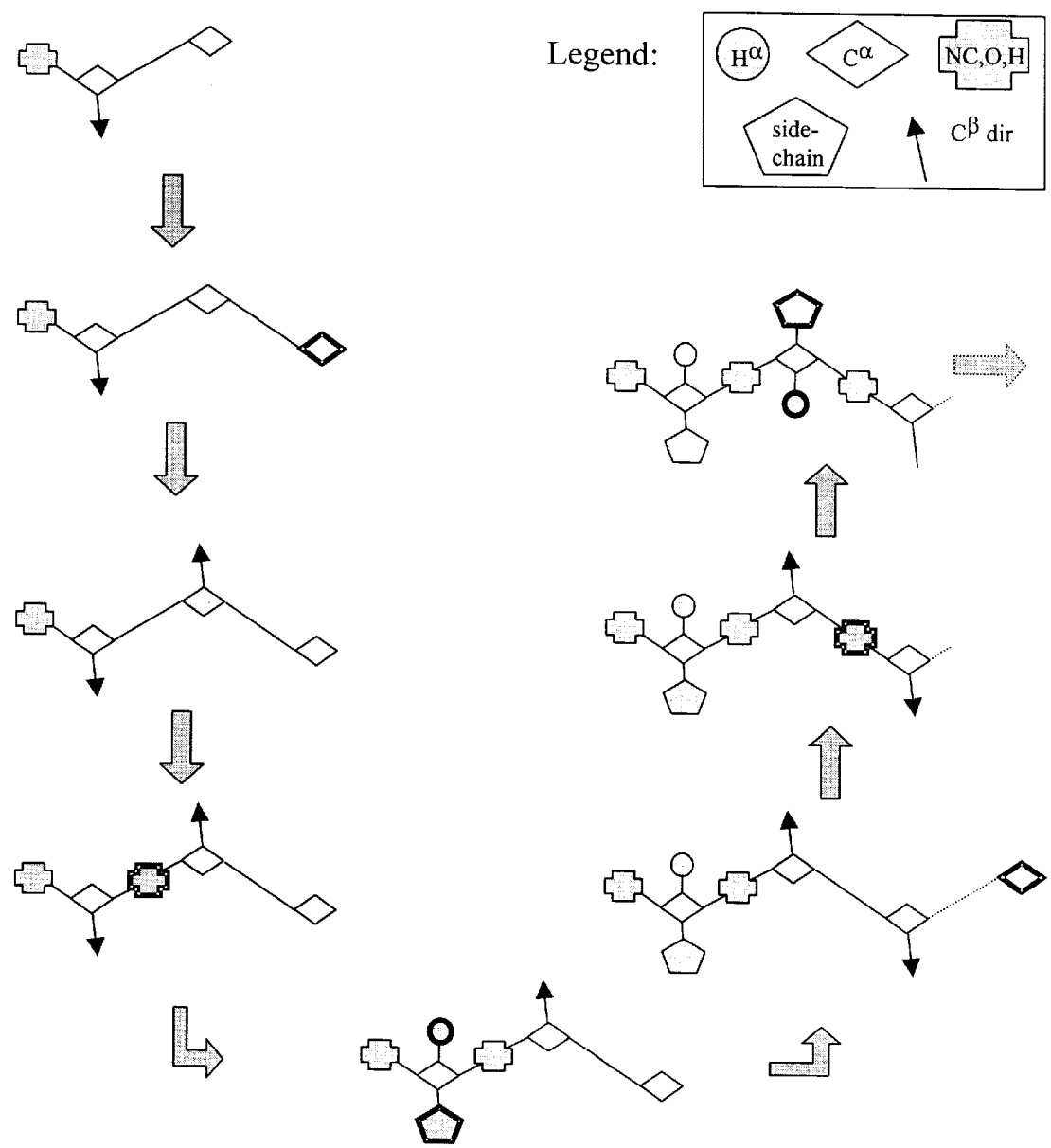
FIG. 1 is a schematic diagram of a method of the invention.

As hereinbefore mentioned the invention provides a method for creating an ensemble of conformations of a protein of known or unknown structure. The method involves constructing a backbone structure of α-carbons of the protein by adding and removing carbon atoms through chain elongation and backtracking where the backtracking removes an atom if it is closer to its neighbor than allowed by van der Waals radii.

An atom is positioned in the α-carbon backbone using a trajectory graph data system. A "trajectory graph" or "trajectory distribution" is a two-variable description of the relative angular space that a single amino acid can occupy in a protein, with an orthogonal arbitrary axis indicating the frequency at which that trajectory is sampled. The angular space is a projection of the spherical distribution of the possible positions into which the $i^{th}$ alpha carbon can be placed independently relative to the i−1, i−2, and i−3 residues at the end of a growing chain. All conformations available to each amino acid can be sampled using this system. A nonredundant database may be used to seed the initial trajectory graphs for each amino acid type providing a statistical sampling, for each kind of residue, of the conformational space they are observed to visit in native proteins. For a protein backbone of N residues, the backbone conformation graph may be established for the protein which comprises a linear set of N trajectory graphs, each one corresponding to one amino acid.

Database-derived trajectory graphs can be resolved into alpha, beta, and coil secondary structure components for each amino acid type. The GOR ((Gamier J, et al,. J. Mol. Biol. 1978;120:97–120 and Gamier J, et al Methods Enzymol. 1996;266:540–553) secondary prediction method may be used to recombine the normalized secondary-structure based trajectory graphs in predicted proportions (e.g. 70% alpha-helix, 20% beta-sheet, 10% coil) for each amino acid in the sequence, which when combined will form a starting backbone conformation graph. A statistical method for secondary structure prediction is incorporated at the beginning of ensemble sampling. Since these methods provide at least 60% accuracy, it will reduce the conformational searching at the beginning of the simulation, reducing the scope of the computation. It will also allow predicted secondary structure to be sampled in a flexible, probabilistic fashion that will not exclude a possible solution. Empirical potentials of the kind used in threading calculations can be used to score the secondary structure as it is generated across the ensemble and provide additional information to enhance the predictions.

NMR chemical shift information may be directly mapped onto the trajectory graph sampling system described herein. High-resolution NMR chemical data can be used to determine experimental protein backbone (Φ-Ψ angle geometry within a range of about 10 degrees.

The processes and methods of the invention use a backtracking system whenever the chain cannot proceed after a pre-set number of collisions. The number of attempts before backtracking may be varied with the conformational space available at each residue. The backtracking system used in the method preferably utilizes an O(NlogN) algorithm as described herein, to bump-check for van der Waals collisions that is volume independent and easy to maintain in memory as atoms are added and removed during the simulation through chain elongation and backtracking. Backtracking typically allows resampling of the same trajectory graph or distribution. Preferably, the trajectory distribution is broader (versus sharply peaked) to avoid sampling the same amino acid placement again and again.

Sidechain placement may be handled through the use of a sidechain rotamer dictionary (7). Sidechains can be described by very few parameters, generally zero to four ψ dihedral angles, and these themselves only take on a limited range of values, often dependent upon the local backbone conformation at that point. The computer program SCWRL uses such a backbone-dependent rotamer dictionary to add or modify sidechains on backbones (8)

A method or process of the invention may select a set of rotamer coodinates for the sidechain from a pre-computed set of static rotamers, selected at random in a backbone-independent manner; for example, the backbone-dependent dictionaries such as that used by SCWRL, or by self-consistent ensemble optimization (Lee, C., and Subbiah, S., J. Mol. Biol. 1991, 217:373–388) which optimizes a large collection of sidechain conformations simultaneously, iteratively, beginning with an initial guess. Rotamers may also be computed and placed on-the-fly, atom by atom, with arbitrary χ angles; for example, the backbone-dependent rotamer library of Dunbrack (Dunbrack and Karplus, J. Mol. Biol. 1993, 230:543–574; Dunbrack and Cohen, Protein Sci. 1997, 6:1661–1681)) may be used as a sampling distribution function for the placement of rotamers on the fly.

An ensemble of conformers generated using the method of the invention may be directed to re-visit favourable conformations through the use of the trajectory graph data structure described herein, together with a weighting scheme and scoring function. Information about what parts of conformational space are favorable or unfavorable may be extracted and recorded in the trajectory graph data structure as described herein and passed directly onto the mechanism that generates individual protein structures in the next ensemble. Therefore, each iteration in a simulation is an entire ensemble of, for example, 1000 proteins (sufficient to generate a trajectory graph surface), and convergence may be expected within 1000 iterations, for a total of 1 million tested conformations. The system iterates through ensembles until the controlling backbone conformation graph stops changing shape. This objectively allows folding to proceed as well as allowing unstructured regions to remain in the ensemble as they do in nature.

A crease weighting feedback system may be used with the trajectory graphs. Crease weighting uses the arbitrary sampling frequency axis on the trajectory graph. The system is akin to making a crease in the trajectory graph so that the next iteration visits this structure again. For example, a protein backbone forming a loop may be revisited more often in the next ensemble.

The conformational space available to a protein folding ensemble may be confined based on data from electron microscopy or atomic force microscopy. These techniques generate volume data files (polygon surfaces) that may be incorporated into the simulations as confining volumes. This will further restrict the conformational space sampling and provide a method for fitting proteins into microscope-derived volume data.

Available scoring schemes used as predictive functions for protein folding may be used in the present invention. For example, a coarse amino-acid scoring scheme as described by Godzik, A. (Structure, 15:363, 1996) or a fine atomic scoring scheme (Zhang C. et al, J. Mol. Biol. 267: 707, 1997) may be used in the present invention. A scoring mechanism based on fitting all sidechain rotamers simultaneously into the space of an individual residue may also be utilized. The number of non-colliding rotamers reported for each residue may be enumerated as a fraction of its close residue-residue contacts. For example, if 4/6 rotamers of tryptophan are bumping neighboring contacts, and the tryptophan has 5 close amino acid contacts, it scores 0; similarly if none of the rotamers fit in the space it scores 0.

Once a three-dimensional model has been generated using the techniques described herein it should be analyzed to determine its correctness. A computer program available to assist in this analysis is WHAT_CHECK. The entire structure may be further refined. Refinement may consist of energy minimization with restraints, especially for the sidechains.

The method of the invention is preferably implemented as a computer program stored on a storage media or device readable by a computer, for configuring and operating the computer when the storage media or device is read by the computer.

While the methods and processes of the invention may be used in identifying favourable conformational spaces in an ensemble of conformations of a protein, the methods and processes may also be used to predict structures to aid in screening and development of diagnostic and therapeutic proteins or portions thereof in rational drug design, to search for analogues of known protein structures, or to aid in an analysis of biological function and activity.

The following non-limiting examples are illustrative of the present invention:

EXAMPLES

Example 1
Speeding Up Nearest-neighbor Calculations With a Novel Hierarchical Tree Structure: The binary-d Tree Computer modeling of large polymers shares similar inefficiencies with those of particle simulations (Boris, 1986; Lambrakos and Boris, 1987), celestial mechanics (Ambrosiano et al., 1988; Appel, 1985; Greengard et al., 1987), and neural networks (Omohundro, 1987). These are collectively known as N-body problems. A system of N entities forms an N-body problem when each entity contributes a force or a property that influences all the other N-1 entities. The total number of pairwise interactions for these systems is $N(N-1)/2$. The computational time required to solve for each additional entity increases as $N^2$. For systems with large N or with many $N^2$ dependent relations, such calculations dominate CPU time (Van Gunsteren, 1984).

Approximations have been made to improve the computational efficiency for such systems. For properties which are distance dependent, it is most useful to find nearest neighbors. The general criterion for an optimized solution is that it quickly finds the nearest neighbors to each entity in the system. For distance dependent systems, near neighbor calculations have been accelerated using neighbor lists (Van Gunsteren, 1984), grid techniques (Boris, 1986; Lambrakos and Boris, 1987), or hierarchical data structures such as binary trees (Appel, 1985), and oct-trees (Omohundro, 1987; Barnes and Hut, 1986; Karfunkel and Eyraud, 1989). Hierarchical structures have been identified as the most efficient of these (Omohundro, 1987; Hernquist, 1988; Katzenelson, 1989).

The data structure used here is a binary tree in one-dimension. The difference between this structure and the oct-tree or the k-d tree (Omohundro, 1987) in higher dimensions is that it is comprised of points or vectors, rather than partitioned volumes or hyper-rectangles. It is also memory efficient requiring only 2 pointers for each dimension (2d), rather than $2^2$ pointers for quad-tree or oct-tree systems. A program which employs the binary-3 tree to generate polyalanine structures using a kinetic, self-avoiding random growth model is used as an example of the speed of this data structure.

Figure 2A:
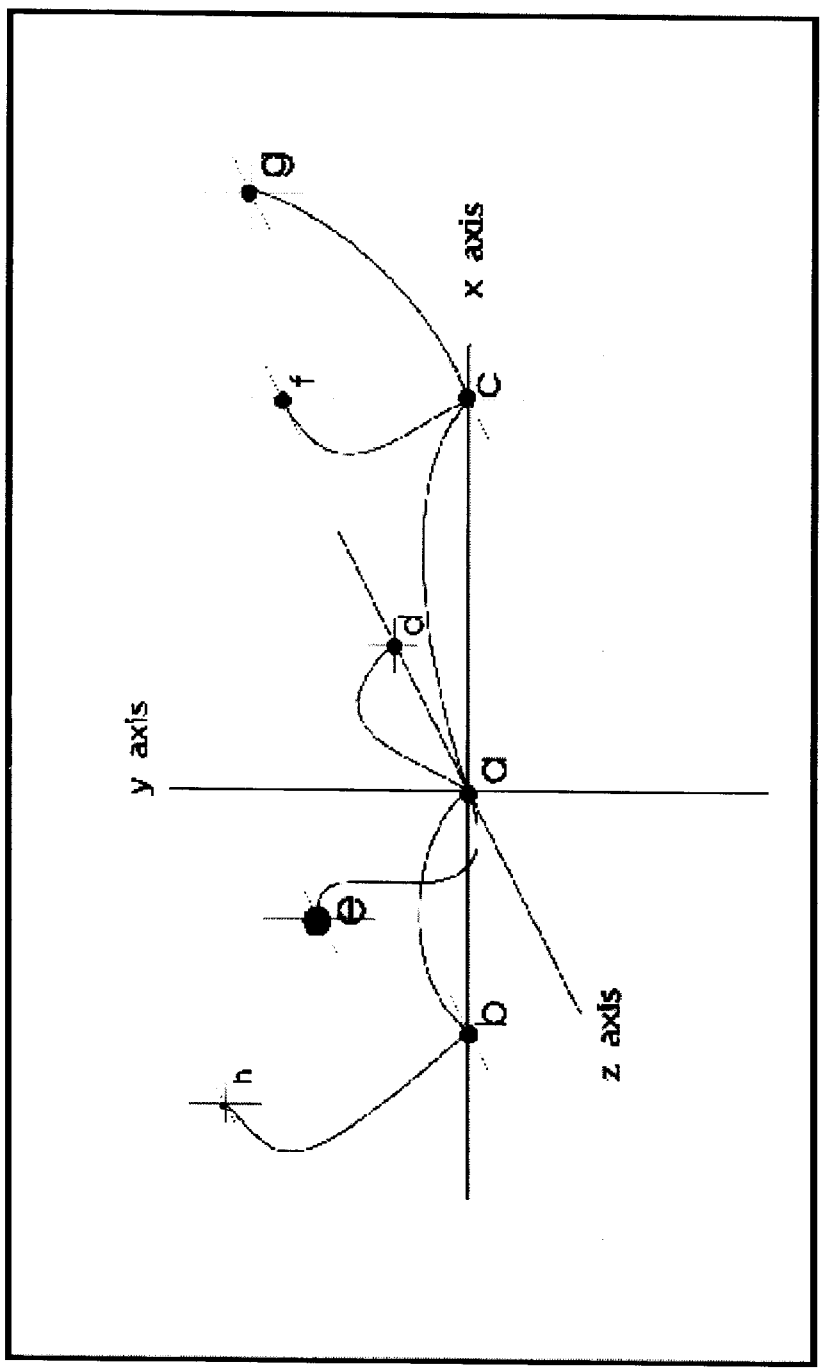
FIG. 2 shows the insertion of the points a(0,0,0), b(−4,0,0), c(8,0,0), d(0,0,2), e(0,4,3), f(6, 3,−4), g(9,5,0), and h(−70, −90, −30) in sequence forms the binary-d tree depicted in FIG. 2A as a three-dimensional representation of the points in space connected by their pointers, and (FIG. 2B) as a tree showing the node structure and how the pointers interconnect. Node c may be easily removed and its children reattached by simply inserting them back into the tree.

The binary-d tree is illustrated in FIGS. 2A and B. The recursive tree building algorithm is shown in Listing 1 for the three-dimensional case, but is easily expanded to other dimensions.

The node in this example has two arrays. The first array Dim[ ] holds the X, Y, and Z coordinates. It is indexed with 0 for X, 1 for Y, and 2 for Z. The array of pointers to further NODEs, Way[ ], represents the six left and right child pointers. These are indexed from 0 to 5. With these arrays and indices, the left child pointer of the nth-dimension is WAY[(n−1)*2] and the right child pointer is Way[(n−1)*2+1]. The procedure PUTIN is called with three arguments: NewNode—a pointer to the NODE to be inserted into the tree; TreeNode—a pointer to the NODE in the tree with which NewNode will be compared; and dimension—the index of the dimension at which to begin the comparison. Lines 4–14 act to select the branch from TreeNode where NewNode would be attached to the tree. The values of the coordinates are compared, starting from the dimension which was passed to the procedure. If the NewNode value is greater than the TreeNode value, the right child branch index is generated for the variable branch. If it is less, the left child index is formed. Importantly, if they are equal, then the next dimension is indexed and the comparison is repeated. (In practice, equality is evaluated using some value for the desired threshold of precision.) If all three coordinates are equal, PUTIN will not insert the node (line 15). Once a branch is selected, its pointer is tested for occupancy (line 17). If it is free, NewNode is attached to the tree (line 18). If it is occupied, TreeNode is moved to the node at that branch and PUTIN is called recursively. Once the tree of data points is formed, it can be used to test for near neighbors with a three-dimensional branch and bound process. One recursive form of the code which can execute a three-dimensional branch and bound search using the binary-d tree is listed.

Three related recursive routines are used: XNeighbor, YNeighbor, and ZNeighbor. The boundary nodes MinNode and MaxNode describe a three-dimensional rectangular probe volume, as in FIG. 3(d). In procedure XNeighbor, lines 2 and 3 traverse the tree recursively to the leftmost node within the boundary, in the first dimension. Then the next dimension's branch and bound routine, YNeighbor, is called. Finally, lines 5 and 6 perform the rightward branching. Procedures XNeighbor and YNeighbor are identical, but have different dimension indices. Procedure ZNeighbor is also like XNeighbor, but contains the complete test for the probe volume (ZNeighbor lines 4–9) instead of line 4. This is necessary since all three coordinates must be tested simultaneously to determine if the point is contained in the rectangular prism range MinNode to MaxNode. Line 9 of ZNeighbor contains a call to a routine ReportNeighbor, which can report or list the nodes encountered in the probe volume. If ReportNeighbor builds a list of these nodes as they are encountered, they will be sorted in back to front order by the branch and bound process itself. Any test of nearest neighbors that requires a non-rectangular test volume should use the branch and bound routine with a rectangular prism shaped volume enclosing that volume. Nearest neighbors found in the volume, can be further tested with euclidean distance calculations.

Simulation of 50–3000 mer random walk pseudoproteins ($\alpha$-carbons only) (Flory, 1989) on a 80286 based microcomputer was undertaken to demonstrate the speed of the algorithm. In order to extend the chain for each amino acid, a point was randomly generated on the surface of a sphere corresponding to possible positions of the $\alpha$-carbon of an amino acid. This sort of random walk is meant to describe a growing polypeptide chain with uniform monomers. Such walks have been described as "growing" (Lyklema, 1984) or "kinetic" (Majid et al., 1984; Pietronero, 1985) self-avoiding walks. The distance from an inserted $\alpha$-carbon to the penultimate $\alpha$-carbon was constrained to lie between 4.5 and 7.2 Å. This makes the average angle between the $\alpha$-carbons 107.1°. A rectangular test volume of 7.26 Å centered at the new $\alpha$-carbon was then searched using the branch-and-bound routines. Any $\alpha$-carbon found within this test volume constituted an occurrence of self, so the coordinates were discarded. An empty test volume resulted in the addition of the $\alpha$-carbon to the chain and the insertion of the coordinates into the tree.

Figure 4A:
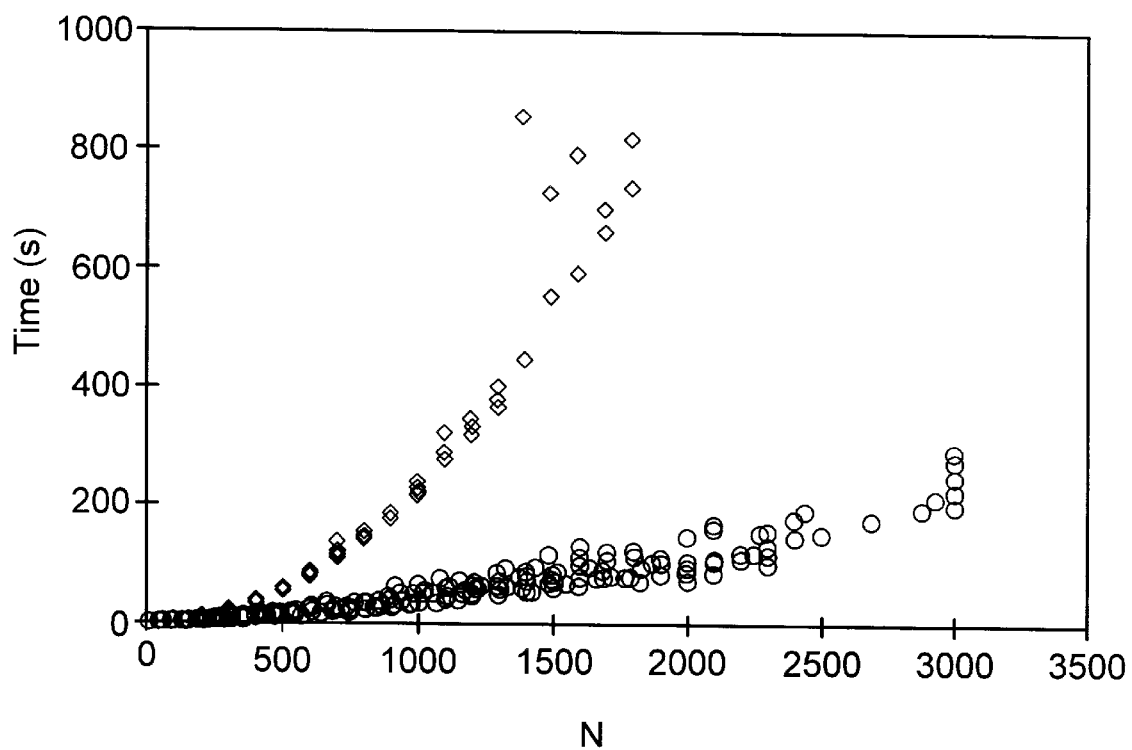
FIG. 4 are graphs showing (FIG. 4A) Time versus number of α-carbons (N) of the $N^2$ computation (diamonds) and the binary-d tree based computation (circles).
(FIG. 4B) Plot of Time versus (TlogT), where T is number of attempts to insert a new α-carbon, demonstrating that the algorithm behaves as O(NlogN).
Figure 4B:
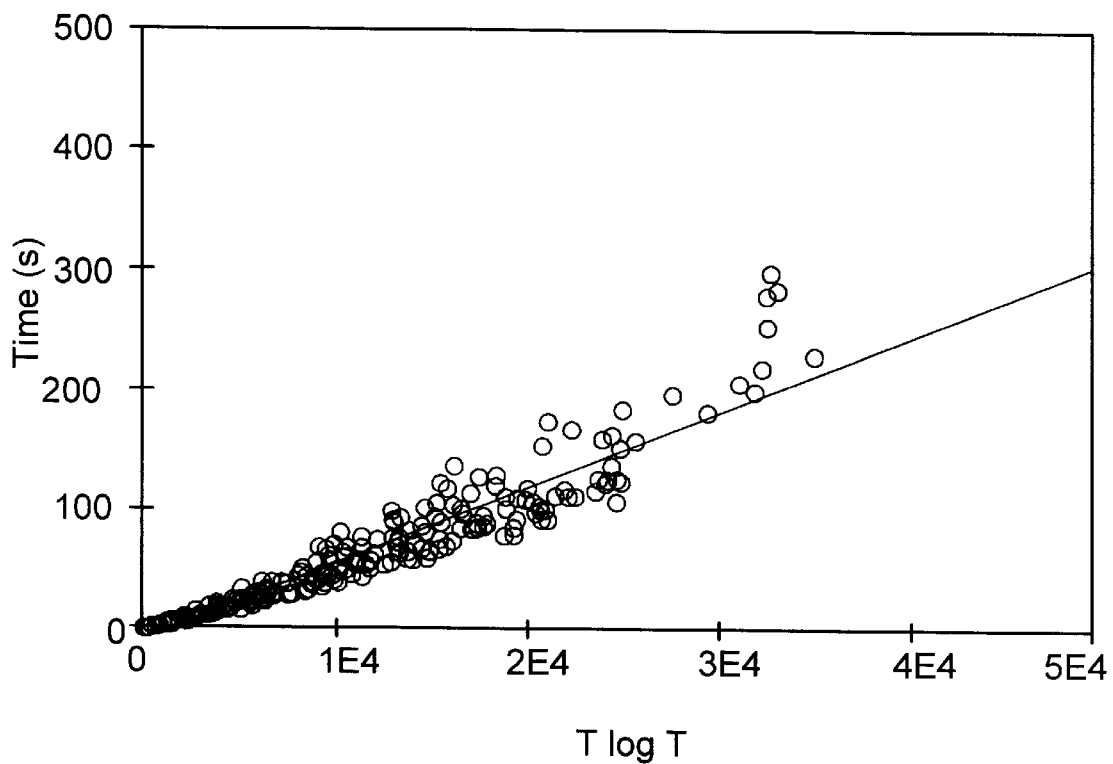

FIG. 4A shows the speedup effect of the algorithm over the $N^2$ computation run on the same hardware, compiled with the same software. With as few as 200 points in the pseudoprotein the binary-d tree requires half the amount of time as the $N^2$ process. In order to demonstrate the O(NlogN) dependence of the algorithm, it was necessary to consider the time taken by discarded $\alpha$-carbons. The number of attempts to insert a new $\alpha$-carbon (T) is plotted as time vs TlogT in FIG. 4B.

Upon inspection of the branching of the binary-d tree, the discrimination is based almost entirely on the first dimension. Hence a binary tree of the first dimension's coordinates presents a similar speedup. This is the general case with well separated points with high precision coordinate values. Higher dimensions in the data structure are used only when degeneracy is detected in an earlier dimension. This depends upon the resolution used to measure equality of position. For the atomic models presented here, the resolution should be small compared to the diameter of the atoms. The smaller the resolution, the less the higher dimensions of the tree are used. A binary-d tree with a coarse resolution (e.g. half an atomic diameter) can miss some near neighbors.

The binary-d tree's higher dimensions could be used much more efficiently if the resolution was imposed by a grid or lattice. In the case of integer three-dimensional space, the process of insertion of a point into a binary-3 tree reveals any prior occupant of that point without the branch and bound process. A binary-2 tree should provide sufficient segregation for nearest neighbors searches with most three-dimensional atomic data. A binary-4 tree could be used to encode time as well as three-dimensional position, allowing for time and space resolution of nearest neighbors, such as those important in celestial mechanics.

Despite the inefficiency in the use of the higher dimension pointers of this tree structure, a node in a binary-d tree has 2 fewer pointers than the corresponding oct-tree node. In addition, this tree is completely independent of previous partitions, unlike the oct-tree. A node can be removed, and its child nodes re-linked to its parent node, as with a binary tree. Hence the tree can change dynamically, which is useful for localized or segmental motions. Optimizations such as tree balancing can also benefit this data structure (Knuth, 1973). The branch-and-bound algorithm can rapidly return a list of points in a given volume in back-to-front order. This means that hidden-line removal, clipping, and ray tracing could be implemented with the binary-d tree.

Listing 1

```
TYPE DECLARATIONS
NODEPOINTER (->NODE)
{notation -> indicates "points to"}
NODE {
        array of real            Dim[0. . .2]
        array of NODEPOINTER     Way[0. . .5]
     }
PROCEDURE PUTIN
ARGUMENTS
    NODEPOINTER NewNode
    NODEPOINTER TreeNode
    integer dimension
VARIABLES
    integer d
    integer branch
    BEGIN
    1    branch = -1
    2    d = dimension
{the following determines the dimension for branching}
    3    Do
```

-continued

Listing 1

```
       4        IF (NewNode->Dim[d] > TreeNode->Dim[d])
       5        THEN
       6           dimension = d
       7           branch = (d * 2) + 1
       8        ELSE
       9           IF (NewNode->Dim[d] < TreeNode->Dim[d])
      10        THEN
      11              dimension = d
      12              branch = d * 2
      13        d = d + 1
      14   WHILE ((d <= 2) AND (branch = -1))
{based on the branch, traverse the tree or insert NewNode}
      15   IF (branch >= 0)
      16   THEN
      17        IF (TreeNode->Way[branch] = NIL)
      18        THEN TreeNode->Way[branch] = NewNode
      19        ELSE
      20           TreeNode = TreeNode->Way[branch]
      21           PUTIN (NewNode, TreeNode, dimension)
       END
GLOBAL VARIABLES
NODE MinNode
NODE MaxNode
PROCEDURE XNeighbor
ARGUMENTS
     NODEPOINTER TreeNode
       BEGIN
       1     IF (TreeNode NOT = NIL)
       2         IF (TreeNode->Dim[0]> MinNode->Dim(0))
       3         THEN XNeighbor(TreeNode->Way[0])
       4         YNeighbor (TreeNode)
       5         IF(TreeNode->Dim[0] < MaxNode->Dim[0])
       6         THEN XNeighbor(TreeNode->Way[1])
       END
PROCEDURE YNeighbor
ARGUMENTS
     NODEPOINTER TreeNode
       BEGIN
       1     IF (TreeNode NOT = NIL)
       2         IF (TreeNode->Dim[1] > MinNode->Dim[1])
       3         THEN YNeighbor(TreeNode->Way[2])
       4         ZNeighbor (TreeNode)
       5         IF(TreeNode->Dim[1] < MaxNode->Dim[1])
       6         THEN YNeighbor(TreeNode->Way[3])
       END
PROCEDURE ZNeighbor
ARGUMENTS
     NODEPOINTER TreeNode
VARIABLES
       integer d
       integer found
       BEGIN
       1     IF (TreeNode NOT = NIL)
       2         IF (TreeNode->Dim[2] > MinNode->Dim[2])
       3         THEN ZNeighbor(TreeNode->Way[4])
       4         found = TRUE
       5         FOR d = 0 TO 2 DO
       6     IF ((TreeNode->Dim[d] > MaxNode->Dim[d])
               OR (TreeNode->Dim[d] <= MinNode->Dim[d]))
       7         THEN found = FALSE
       6     IF (found = TRUE)
       9     THEN ReportNeighbor(TreeNode)
      10     IF(TreeNode->Dim[2] < MaxNode->Dim[2])
      11     THEN YNeighbor(TreeNode->Way[5])
       END
```

Example 2
An Efficient, Validated "Folding-funnel" Method For All-atom, Real-space Protein Conformer Sampling, Capable of Reconstructing Known Protein Folds
Materials and Methods
Molecules in Memory The random protein generator (also sometimes referred to as FOLDTRAJ, and INITTRAJ which generates the input trajectory distribution field for FOLDTRAJ) was programmed completely in ANSI C using the MMDB-API (Molecular Modeling DataBase Applications Programming Interface)(9) and the NCBI (National Center for Biotechnology Information) toolkit (10)). This allows the software to be compiled on most popular systems including Win32, Linux, IRIX, and Solaris. The CodeBase (Sequiter Software, Edmonton, Alberta, Canada) C database library was used as well as bzip2 compression (Seward, J. v. 0.90 1998) in order to handle the very large files that are used as the input probability density functions.

Input to the program takes the form of a simple text file containing the sequence to be folded, using the one-letter amino acid abbreviations. Several text files containing various configuration parameters are read in each time the program is executed as well. Under the MMDB-API system a complete chemical graph of each molecule (only one in this case) is contained in memory, with all bonds explicitly present. The MMDB-API data structures allow two levels of coordinate degeneracy: each atom can have multiple co-ordinates, each with a different occupancy value (whose sum should be 1.0); and multiple models can exist, as in NMR structures. The multiple-coordinate degeneracy can be used to hold any number of rotamers, on a single backbone conformation, and the occupancy term can be used to assign each rotamer a probability. For the present illustration of generation of random proteins, none of these degeneracies are used. However, the program can be further developed so that rotamer placement is no longer random but based upon energy scores and steric clashes. Output from the program is a protein structure in NCBI's ASN.1 format or PDB format.

Non-Redundant Set of PDB

The majority of statistical data from the Brookhaven Protein Data Bank (PDB) (Bernstein FC, et al, J. Mol. Bio. 1977;112:535–542) used in this work was obtained from a non-redundant set of the PDB. The nonredundant set provided by NCBI was used. A representative structure (or chain, where appropriate) was selected manually at NCBI for each of the 1255 resultant groups using a BLAST p-value cut off of $10^{-7}$. This list was further culled by removing entries less than 40 residues in length, chains containing "unknown" residues and those with X-ray resolution greater than 3.0 Å. Chains of less than 200 residues were limited to 2.5 Å resolution. Finally, those missing residues or coordinates were removed, resulting in a final non-redundant set of 834 protein chains.

O(NlogN) Collision Detection

In order to create realistic random protein structures, a kinetic, self-avoiding random walk (11) was used. This differs from a standard random walk in two ways: self-intersections are not allowed, where each vertex along the walk is presumed to have some non-zero volume; and the walk is kinetic. This means that if a collision occurs, the walker will backtrack to the previous step, and try again, until an allowable location for the next step is found. Polymer theory (12) suggests that self-avoidance introduces bias into a random walk, and classically the walk is restarted from scratch if a collision occurs.

During the random walk and protein construction then, if any two atoms are closer than allowed by van der Waals radii (8) a hard-sphere collision is deemed to occur. The most recently added residue would be removed and a new location chosen for it. In order to quickly test for collisions in three dimensions between new atoms and their nearest neighbors, a novel hierarchical algorithm, the binary-d tree (see Example 1), was employed and tested for finding nearby neighbors to a given point. A small one-time overhead of adding each new point to the tree, and removing them when forced to back up, ensures a rapid collision-test lookup later on.

Nearest-neighbor measurements to perform bump-checking can easily bog down the protein structure generation, as this system represents a classical N-body problem. A system of N entities forms an N-body problem when each contributes a force or property that can influence all other N−1 entities, as the total number of interactions is N(N−1)/2. The computational time dependence of such a system increases as $O(N^2)$, and such computation can grow to dominate CPU time (16). Few protein structure generation methods report analyses of their time-complexity with N.

Algorithms to improve the computational efficiency of N-body systems include using neighbor lists (16), grid techniques (17), or hierarchical data structures such as binary trees (18) or oct-trees (19–21). Hierarchical structures have been identified as the most efficient of these (19;22;23) but are not routinely used in molecular simulations as are grid techniques. There was an interest in implementing an O(NlogN) algorithm for bump-checking van der Waals collisions that was (a) volume independent and (b) easy to maintain in memory as atoms are added and removed during the simulation through chain elongation and backtracking.

Figure 2B:
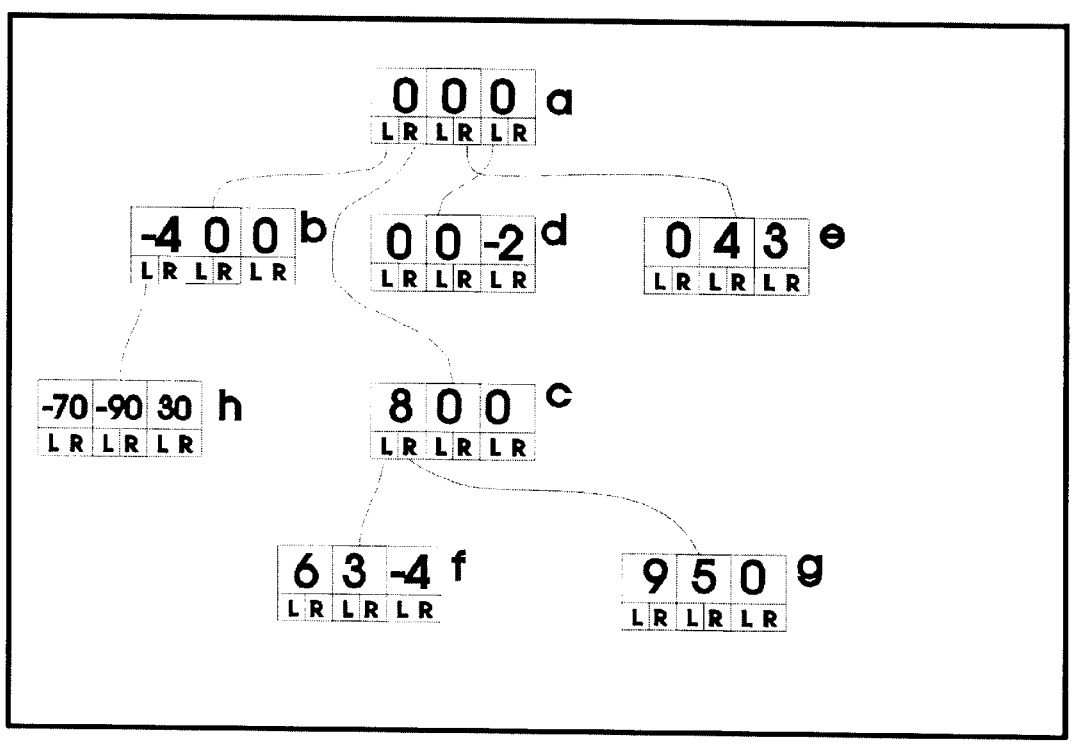
Figure 5:
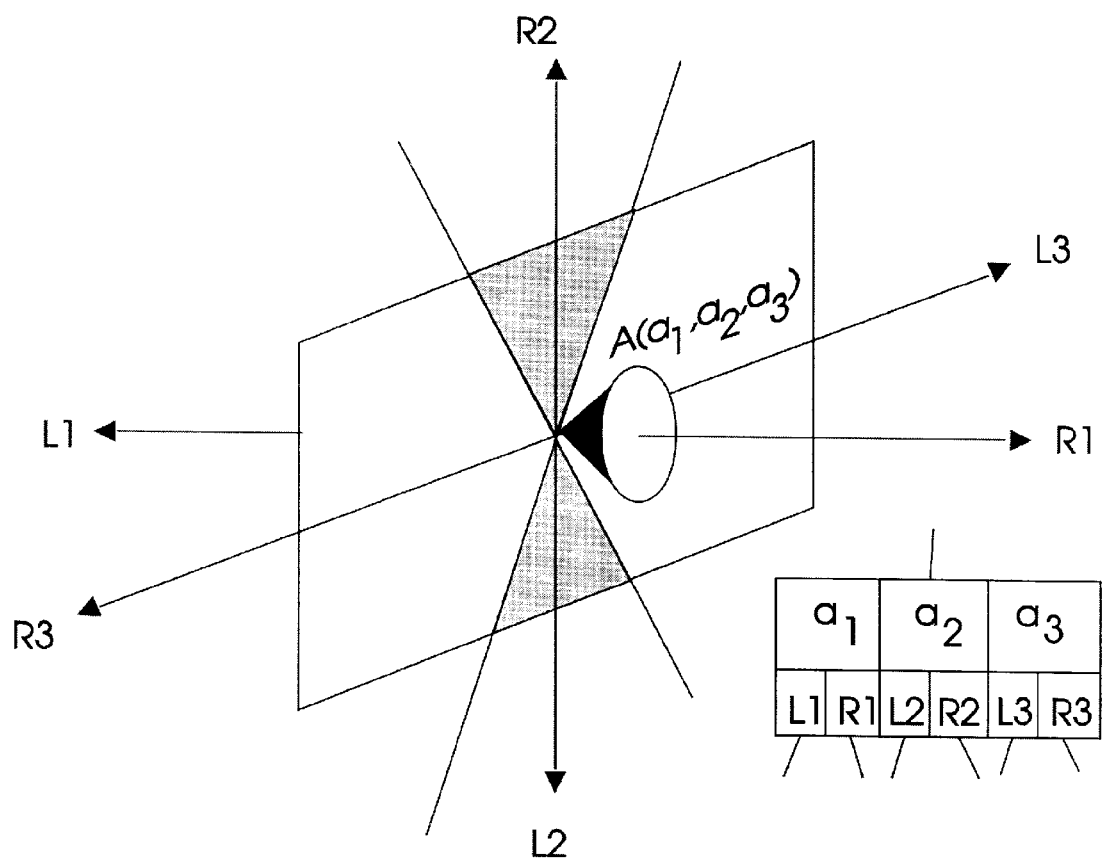
FIG. 5 shows the node structure of the binary-d tree. Note that the left and right child pointer pairs {L1,R1}, {L2,R2} and {L3,R3} are simply binary trees that descend down 3, 2, and 1 dimensions.

The algorithm developed by the present inventors, based on a hierarchical data structure, partitions atoms in a molecular scene into nodes, as shown in FIG. 5, representing points in space relative to one another in a multidimensional tree, rather than enclosing them in some fixed volume as do oct-tree or grid methods. Unlike the oct-tree, this tree does not need to pre-declare a fixed volume in which the protein structure is to be made. The tree is referred to as a binary-d tree, since it is actually a binary tree in the first dimension, and conceptually could be used in other higher dimensions i.e. it could be extended into d binary trees at each node as shown in FIGS. 2A and 2B. The binary-d tree has nodes pointing to atomic coordinate locations, together with a set of three pairs of left/right child pointers. The difference between this tree and the oct-tree or k-d tree (19) is that it is comprised of points or vectors, rather than partitioned volumes or hyper-rectangles. It is also memory efficient, requiring only 2 pointers for each dimension (2d), as opposed to $2^d$ pointers for oct-trees. In practice, a small one-time overhead is paid when adding each new atom's coordinates to the tree. Importantly, coordinates in this tree can be removed with only minor adjustments to the child nodes. This is useful when backtracking, as atoms can be removed without having to rebuild the entire tree.

Figure 3:
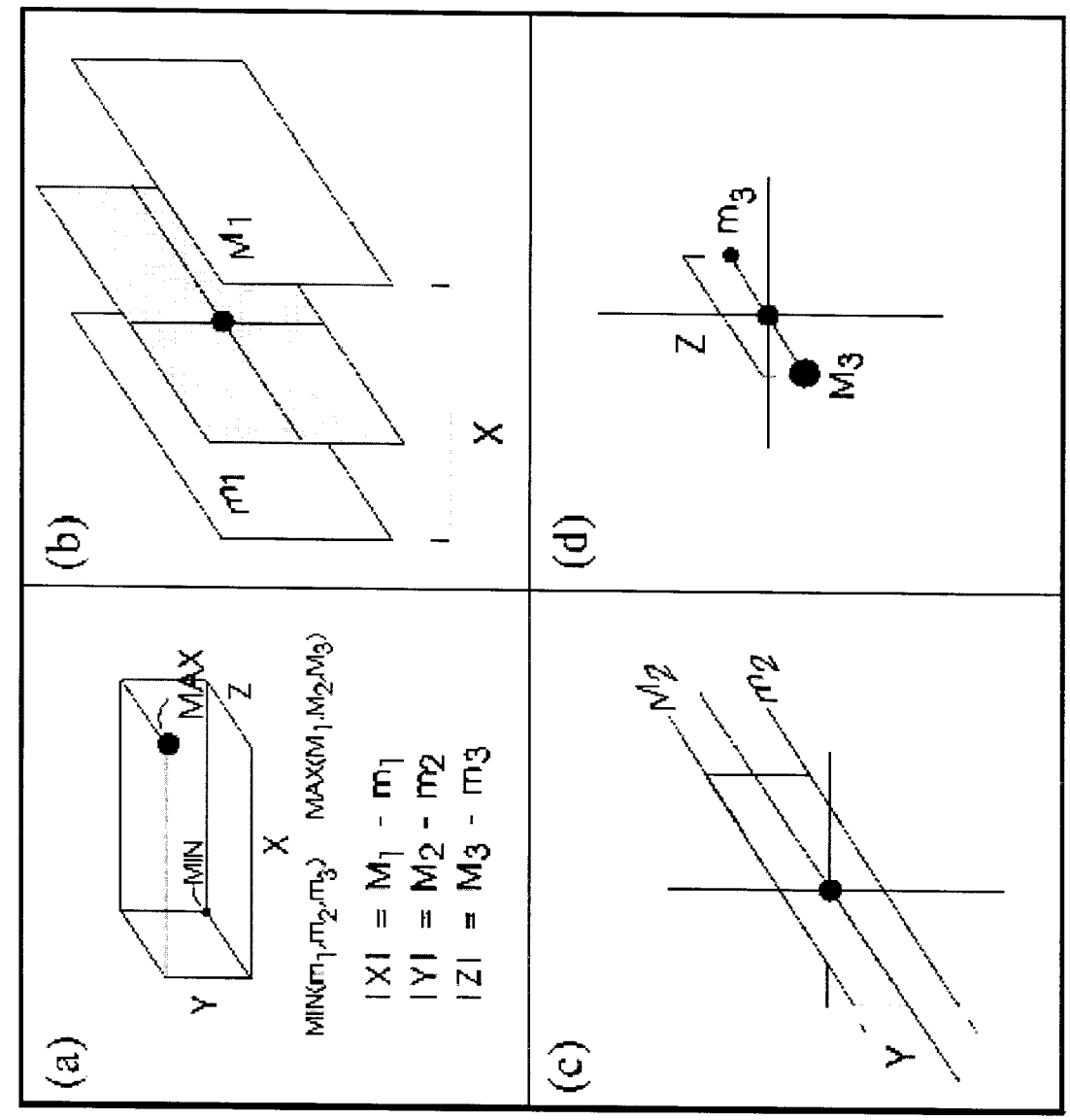
FIG. 3 shows the three-dimensional branch and bound search process. A search volume is designated by two points $MIN(m_1,m_2,m_3)$ and $MAX(M_1,M_2,M_3)$. These form a rectangular prism (a) with sides parallel to the xy, yz, and xz planes. (b–d) shows the elimination of (b) planes orthogonal to x containing points in the tree that are not in the range $m_1..M_1$; (c) lines on each plane containing points perpendicular to y that are not in the range $m_2..M_2$; and (d) points on each line that are not in the range $m_3..M_3$. (b), (c), and (d) correspond to the procedures XNeighbor, YNeighbor, and ZNeighbor.

Nearest neighbors in the tree are obtained by probing the tree with a multidimensional search using boundary coordinates that describe a three-dimensional rectangular probe volume shown in FIG. 3. The search returns a list of the atomic coordinates found in the probe volume. The method primarily distinguishes coordinates based on the first dimension, i.e. as a binary tree. The second and third set of left/right child pointers are rarely used. These higher dimensional left/right child pointers provide the key to higher-dimensional discrimination in the case where the first dimension is equivalent, as illustrated in the simple tree in FIGS. 2A and 2B, and add little or no overhead to the implementation or search method. Given the three decimal place precision found in the PDB, it is extremely likely (>99.99%) that any given 100-residue or more structure will have at least two atoms with identical x co-ordinates. The time-complexity of this algorithm was determined to be O(NlogN) with simple α-carbon kinetic random walks, prior to incorporation in the overall method.

Hard/Soft Atoms and H-Bonds

Two models for describing atoms, a hard sphere and a soft sphere approach were experimented with. If any two atoms are closer than allowed by van der Waals radii (Ramachandran GN, et al., Adv.Protein Chem. 1968;23:283–438) a hard-sphere collision is deemed to occur. The most recently added residue would be removed and a new location chosen for it. In order to model van der Waals interactions in a slightly more realistic manner, atoms can be made "soft" by allowing collisions to occur under certain conditions. When a new atom is placed close to an existing one, the sum of their van der Waals radii, R, is compared with the actual distance between them, r. With a hard atom model, the placement is rejected if r<R and backtracking occurs. However, the van der Waals radius is simply an energy minimum for atomic contacts, and is by no means an absolute minimum. Atoms closer together than this energy minimum will only remain so if they cannot push apart because of tight packing in the vicinity, and so there is a smaller chance of occurrence as interatomic distances get smaller. Following the Monte Carlo approach to soft atoms (Gregoret L. M, and Cohen F. E. J. Mol. Biol. 1991;219:109–122), whenever r<R, a random number is used to determine whether the collision is permitted, otherwise, a crash occurs just as in the hard atom model. The further r is from R (with r<R), the greater the chance of a collision.

Whenever one of the two colliding atoms is a hydrogen, and the potential to form a H-bond exists (the colliding atoms and the atom bonded to the hydrogen are either O or N), the angle formed by the two colliding atoms plus the atom bonded to the H is calculated. For a successful H-bond to form, this angle must be between 150° and 180°, and the van der Waals radius of the hydrogen is then reduced by 0.5Å to account for the special bond. If either criteria is not met, the collision is treated as a normal collision as above.

Placement of α-carbons Using the Trajectory Distribution

The goal was to find a method for generating complete chirally-plausible protein structures by choosing from as few variables as possible per residue, combining and enhancing methods conceived earlier for both chain elongation (24), and for positioning β-carbons (4). The peptide backbone atom placement algorithm is a new approach using a binary-search optimization. A geometrical build-up procedure is based on the assumption that by specifying the positions of only the α-carbons in a protein backbone, the remaining co-ordinates can be optimized in a deterministic manner.

Figure 6:
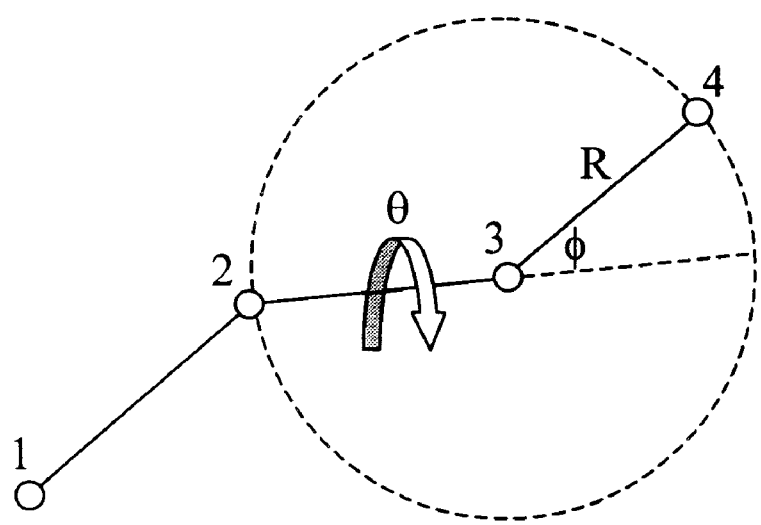
FIG. 6 shows the definition of trajectory space co-ordinates. Given three α-carbons (labelled 1, 2 and 3) the fourth can be placed anywhere on the surface of the sphere of radius R surrounding the third carbon, where R is the inter-Cα distance. The exact position can be specified using spherical co-ordinates φ and θ, as illustrated. φ corresponds to values of latitude ranging from 0 to π, while θ is longitude and runs from 0 to 2π

Given any three consecutive α-carbon co-ordinates, the next one can be specified by its distance R from the previous atom, and its location on the sphere of radius R surrounding the previous atom (FIG. 6). The exact position can be specified using spherical co-ordinates $\phi$ and $\theta$, where $\phi$ corresponds to the azimuthal angle ranging from 0 to $\pi$, while $\theta$ is longitudinal and runs from 0 to $2\pi$. In this case $\theta$ would also be the dihedral angle between the four Cαs and $\theta$, the supplement of the angle between three consecutive Cαs. The distance between consecutive backbone α-carbons is approximately 3.81 Å (or 2.9 Å for a pair where the second residue is cis-proline (4)) which gives R, so that the position of the next residue can be completely determined by choosing only two angles.

In order to randomly generate a complete α-carbon backbone of length N then, N—3 points had to be chosen at random in $\phi$–$\theta$ space (the first three atoms are defined only by the angle between them). The approach used is similar to that of Gregoret and Cohen (24). However, it was realized that in order to allow the sampling of this space, it had to be discretized evenly. The area of a small patch on a unit sphere of size $\Delta\phi$ by $\Delta\theta$ is:

$$\int_{\theta}^{\theta+\Delta\theta}\int_{\phi}^{\phi+\Delta\phi} 1^2 \sin\phi\, d\phi\, d\theta = \quad (1)$$

-continued
$$\Delta\theta(\cos\phi - \cos(\phi + \Delta\phi)) = -\Delta\theta\Delta(\cos\phi)$$

Figure 7A:
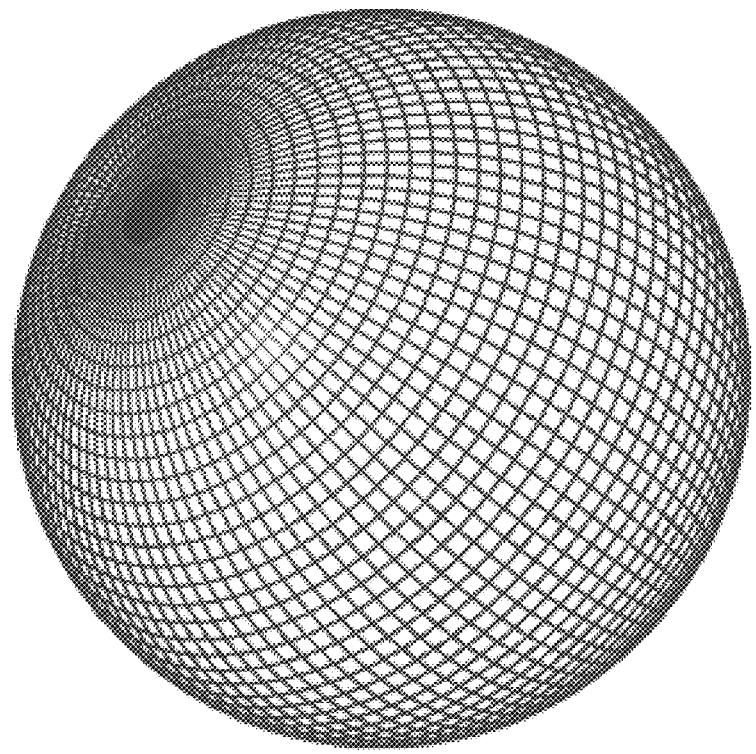
FIG. 7 shows a comparison of a sphere divided equally in both angular dimensions (a) with one divided equally in θ and cosφ, (b) to produce patches of equal area. The latitudinal lines in a) appear to stay almost equally spaced throughout, while in b) they are very closely spaced near the equator, and very far apart near the poles. This compensates for the convergence of the longitudinal lines as they approach the poles, and provides a more unbiased sampling of the spherical surface than a) which tends to cluster samples near the poles, where there are simply more patches per unit surface area.
Figure 7B:
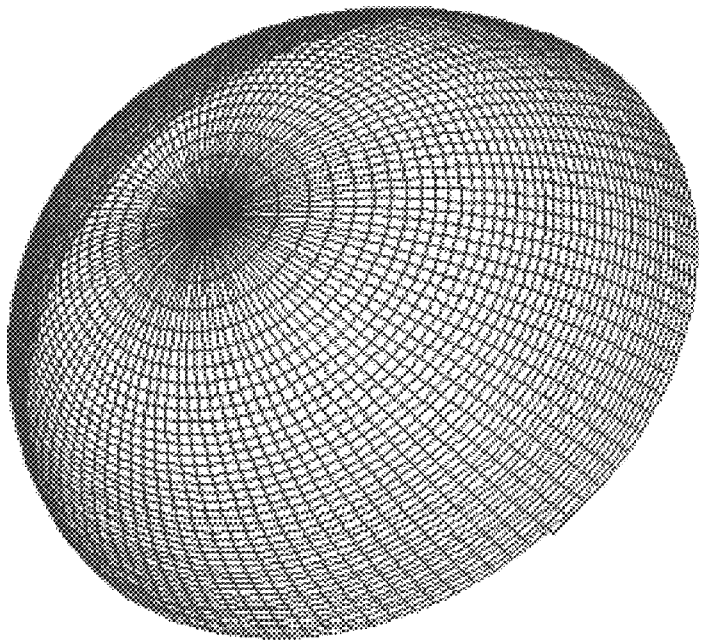

Thus to ensure each discrete unit on the surface of the sphere had the same area, it was required that $\theta$ be divided evenly (in its range from −180° to 180°) and $\cos\phi$ be divided into equal increments between −1 and 1 (FIG. 7). In other words, the value of $\Delta\theta$ must become larger near the poles to compensate for the narrowing in the longitudinal direction and provide a more unbiased sampling of the spherical surface than an even angular distribution, which tends to cluster samples near the poles, where there are simply more patches per unit surface area. This is similar to the problem encountered by geographers when trying to represent the earth on a flat piece of paper. Their solution was the Mercator projection, invented by Gerhardus Mercator in 1568, which projected a sphere onto the inside of a cylinder, which was subsequently unrolled.

By processing the non-redundant set of known protein structures and recording the populations in this angular 2-D space for each residue, based only on residue type, an initial "trajectory graph", "trajectory distribution", or frequency distribution, in this vector space was obtained for each amino acid. This could then serve as a starting point for the random backbone generator, using the frequency distribution function to approximate a discretized probability distribution function (PDF). While processing the nonredundant database, one graph or distribution was produced per residue type, for a total of twenty. When actually beginning the random walk however, one trajectory graph or distribution is maintained for each residue, with its starting value based on residue type alone.

To optimize the speed, the discrete 2-D PDF was represented as a 1-D array and integrated to form the cumulative distribution function (CDF). The value F(x) of the CDF at a given $x_0$ is simply $P(X<x_0)$ where X is the random variable in question. Choosing y as a random number between 0 and 1 and solving for x in the expression F(x)=y provides a fast way to select randomly according to an arbitrary probability distribution. In this implementation the solution to F(x)=y is found quickly by a binary search on the domain of F(x). A simple multiplication then transformed the 1-D position back to this 2-D space to give the "trajectory" to the next point.

Figure 19A:
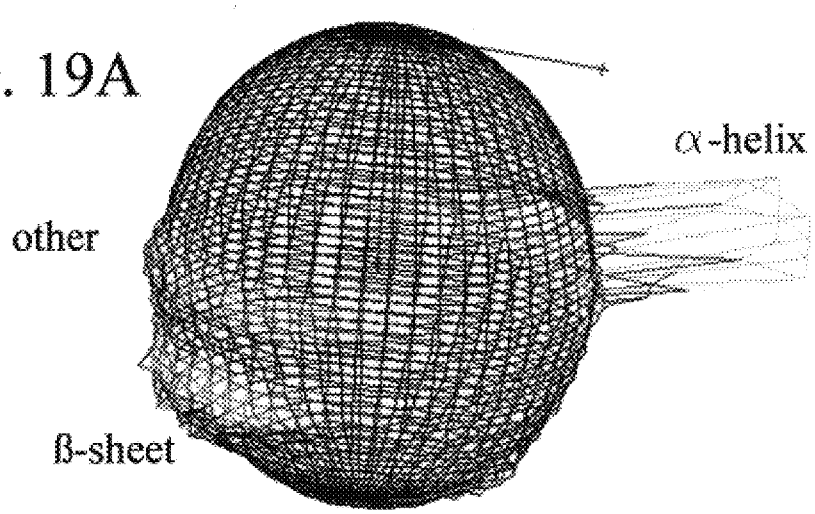
FIG. 19 shows trajectory graphs or distributions as they appear on the surface of a sphere for a) Ala, b) Lys, c) Pro. Each grid square corresponds to a patch of equal area on the surface of the sphere. Peaks for helix, sheet and other are as indicated. Note that while one of the peaks is labeled "other", residues in random coil or turn conformations can actually fall anywhere on the trajectory distribution, including on top of the α-helix or β-sheet peaks. The coloring scheme is intended to give only an approximate indication as to the relative heights of each peak. Note that for Ala and Lys, the helix peak has been truncated for clarity, and as well, only 50 divisions were used in each direction rather than the usual 400. The prime meridian in each figure (i.e. θ=0) is on the right-hand edge of the sphere and the three red dots represent the backbone. $C\alpha_{i-2}$ lies outside the sphere, in the direction of the prime meridian. $C\alpha_{i-1}$ is at the north pole and $C\alpha_i$ is at the center of the sphere. The height of the landscape at any point on the surface of the sphere is hence proportional to the probability that $C\alpha_{i+1}$ will be found there.
Figure 19B:
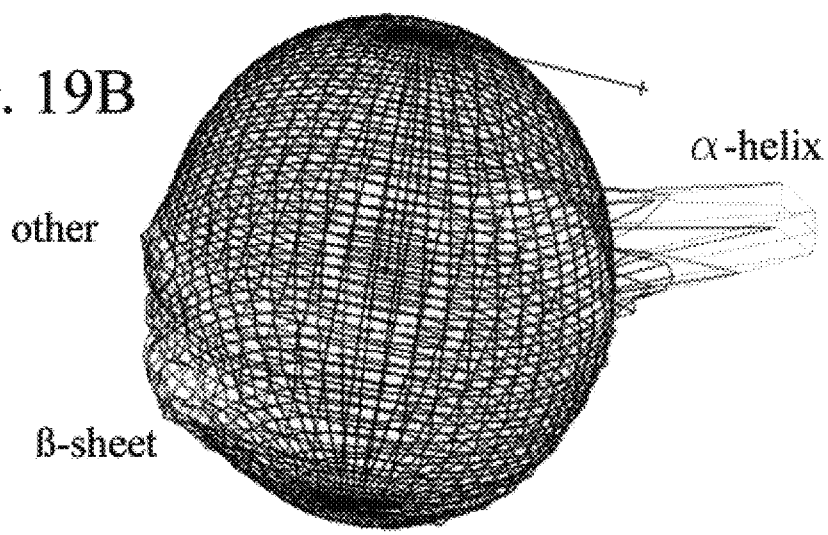
Figure 19C:
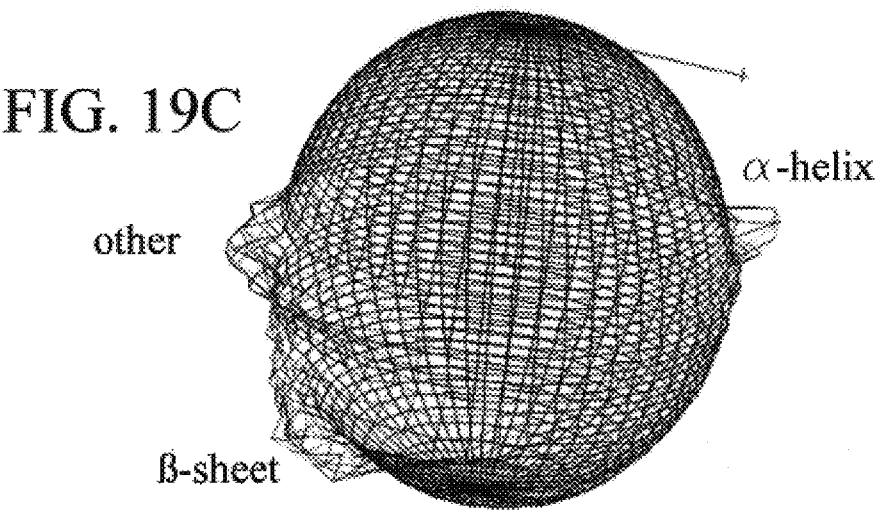

The trajectory distributions as they appear in their native two-dimensional vector space, the surface of a sphere, are shown in FIG. 19. It should be noted that there is no easy way to choose N equally distributed points on a sphere, when N is any integer other than the number of vertices found in the five Platonic solids (Lesk M. Protein Architecture. New York: Oxford University Press; 1991). The best that can be done to get a fair discretization of the sphere is to ensure that each patch has the same area, since, all else being equal, the probability that a patch is chosen is proportional to its area.

Trajectory Distribution Implementation

It was important that the method could accurately represent the α-carbon trace of real proteins since the goal was to represent proteins in continuous space. It was determined that 400×400 discretization of $\cos\phi$–$\theta$ space provided an optimal compromise between backbone precision (measured by Cα—Cα RMSD between actual and "discretized" structure) and memory and disk usage for this sampling system, with 500×500 showing little improvement in quality and 200×200 showing a marked decrease. This requires a rather large amount of data to use as input for this program, especially if all N×400×400 values are loaded into memory at once for a large protein. To deal with this problem a database system was built that contains compressed trajectory distributions as database records, which can be loaded as required for each amino acid being sampled. This database approach affords the extra advantage of buffering, so if the algorithm should backtrack and require a recently loaded trajectory distribution, it may still be in memory and saves the time of loading from disk again.

Figure 11:
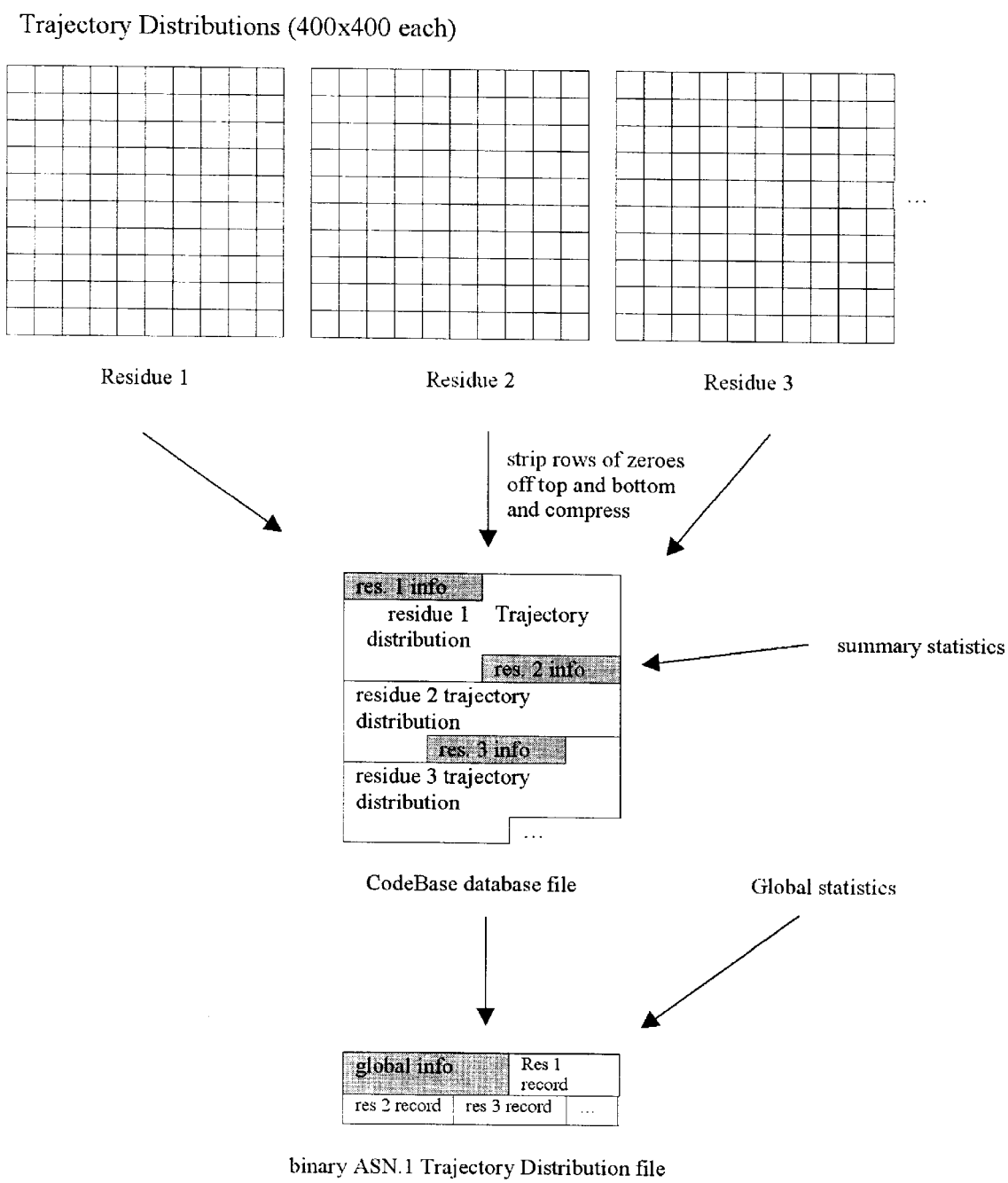
FIG. 11 is a schematic diagram showing the trajectory distributions represented in memory as large 2-dimensional arrays, one per residue. Rows of zeroes at the beginning and end of each trajectory distribution are stripped off, and the remaining data compressed with bzip2 and stored as a CodeBase database record along with other information about the residue (Table I). The entire database, with one record for each residue in the protein it represents, is then packed into a binary ASN.1 file along with some global information such as sequence length and amino acid sequence, and written to disk. It is this "trajectory file" which is used as input to FOLDTRAJ.

Using compression, the amount of space required to store each amino-acid based trajectory distribution was reduced by over a factor of 70. These compressed trajectory distributions were stored as CodeBase binary database records. Additional data about the trajectory distribution was added to database fields, summarized in Table I. The overall scheme is depicted in FIG. 11. While compression time can be lengthy, it need only occur once for each sequence, during the initial creation of the database. Decompression, on the other hand, is nearly instantaneous. The same trajectory distribution binary database file can be used on almost any 32-bit machine (Mac, PC or UNIX) without modification. Finally, to reduce the number of files from three (for a Codebase database) to just one, the files were packed into an Abstract Syntax Notation 1 (ASN.1) binary format file, along with some global information about the protein. Thus the input of the main conformer generator program, FOLDTRAJ, is a single, packaged data file created by a separate program, INITTRAJ.

Placement of β-carbons and Consideration of cis Residues

Rey and Skolnick (4) found that the precise position of the β-carbon (or hydrogen in the case of Gly) was almost completely determined by the positions of the two adjacent α-carbons relative to the one in question and provide a lookup table to locate them. This method was found to work well in most cases, however, at certain locations, especially in short loops between helices or sheets, some (approx. 5–10% of all residues) very poor placements occur that are greater than 0.5 Å from the correct location. Once the Cβ location is known, the placement of the remainder of the sidechain (except for hydrogens) is completely determined by the torsional angles $\chi_1$, $\chi_2$, $\chi_3$, $\chi_4$ of the residue.

Figure 8:
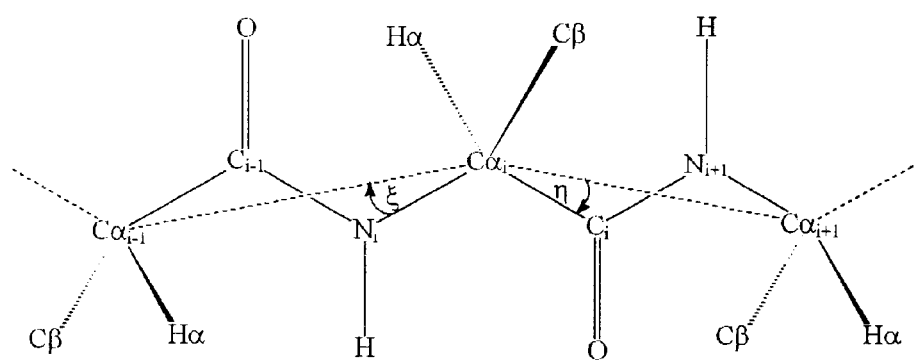
FIG. 8 shows the definitions of the backbone angles ξ and η.

It was necessary to improve on the treatment of cis residues, and the method described herein accurately accounts for the possible addition of cis-prolines. A cis bond greatly affects the virtual backbone angles in the two residues joined by the peptide bond, and not just in the Pro residue, as implied by the tables of Rey and Skolnick. As a result, for a cis bond between residues i−1 and i, different values had to be used for $\eta_{i-1}$, $\xi_i$, angle $O_i$—$C\alpha_i$—$C\alpha_{i-1}$ and length O—$C\alpha_{i-1}$, (see FIG. 8), all of which play a crucial role in the placement of peptide atoms (see next section). As well, the Cβ direction vector at residue i−1 tends to be quite different.

Using the non-redundant set of PDB files, these values were recorded at each occurrence of a cis-Pro, and sorted by amino acid type at the i−1 position. Due to scarcity of the data, Cβ directions were averaged over all $C\alpha_{i-1}$—$C\alpha_{i+1}$ distance bins (i.e. that variable was integrated out in this case) and global averages (independent of amino acid type at residue i−1) of 57.81° were used for $\eta_{i-1}$, 84.46° for $O_i$—$C\alpha_i$—$C\alpha_{i-1}$ and 2.388 Å for O—$C\alpha_{i-1}$. A value of 56.56° was used for $\xi_i$ at cis-prolines. These all had relatively small variation so a global average was a meaningful approximation. Since Cα's are closer across a cis bond as well, a value of 2.955±0.097 Å was derived for the Cα—Cα distance. The Cβ direction cosine thus derived are given in Table II.

As the random walk progresses, there is a 4.63% chance at each Pro residue that it will be placed cis, the observed frequency of cis-Pro in the non-redundant set from the PDB. If a given residue is chosen to be cis, but upon attempt to fill in the atoms, a collision or other error occurs, resulting in backtracking, then upon returning to the Pro, it will again have the same chance to be cis.

Finally, a separate trajectory distribution has been recorded and used for cis-Pro. While presently non-Pro residues are always trans, there is no reason why these could not also be added cis with a certain probability, provided enough data were available to obtain reliable estimates of parameters. Approximately 0.04% of all 175,000 non-Pro residues surveyed in the PDB are in the cis conformation. Similar fractions have been reported elsewhere (Jabs A, Weiss et al., J.Mol.Biol. 1999;286:291–304, and Stewart D E, et al J.Mol.Biol. 1990;214:253–260). This value may be artificially low since residues may be biased towards the trans conformation during crystal structure refinement by software, or manually (Brunger A T. Crystallographic Computing 4. New Techniques and New Technologies. Chester: Oxford University Press; 1988, and Isaacs N. Computational Crystallography. Oxford: Oxford University Press; 1982).

Placement of Peptide Atoms

The remaining backbone atoms were filled in as the random walk progressed from one Cα to the next. In order to locate the peptide C and N atoms, the Cα—C and N—Cα bond lengths (25) were held fixed, and virtual bond angles $\eta$ ($\angle C_i$—$C\alpha_i$—$C\alpha_{i+1}$) and $\xi$ ($\angle N_i$—$C\alpha_i$—$C\alpha_{i-1}$, (see FIG. 8) were chosen to be approximately normally distributed, with means depending on residue type(4) and standard deviation 1.5° since these values vary significantly in real proteins. The peptide dihedral angle ω was fixed at 179.8° on average, with a standard deviation of 1.5°. Under these conditions, the positions of $N_i$ and $C_{i-1}$ were then chosen to minimize the total degrees squared error in $\angle N_i$—$C\alpha_i$—$C\beta_i$, $\angle C_{i-1}$—$C\alpha_{i-1}$—$C\beta_{i-1}$, $\angle N_{i-1}$—$C\alpha_{i-1}$—$C_{i-1}$ and peptide bond length (for Gly, the errors in the angles involving Cβ are taken to be zero). Here error is defined to be the square of the deviation from ideal bond lengths and angles. To account for their different units, the deviation in bond length (in Å) was multiplied by 150, an approximate ratio between standard deviations in the bond angles in question (in degrees) and those in peptide bond lengths (in Å)(25).

Figure 9:
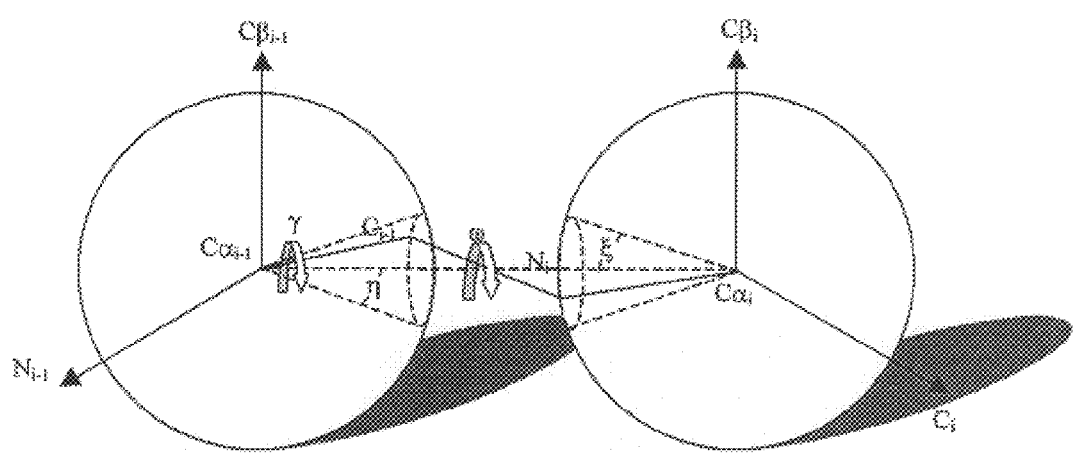
FIG. 9 shows the placement of the peptide C and N atoms. As $C_{i-1}$ is rotated by angle γ about the $C\alpha_i$-$C\alpha_{i-1}$ axis, it traces out the base of a cone of angle η lying on the surface of a sphere, with radius equal to the fixed CαC bond length. $N_i$ is then fixed by ω (the dihedral between $C_{i-1}$, $C\alpha_{i-1}$, $C\alpha_i$ and $N_i$) and the angle ξ, and bond length NCα. The peptide bond length, as well as other backbone angles are not explicitly used, and hence are minimized for changing angle of rotation γ.

The $C_{i-1}$ atom was rotated about the $C\alpha_i$—$C\alpha_{i-1}$ axis, and the other angles and lengths then fixed the position of $N_i$, so that the position yielding the minimum total squared error could be found. The process could be imagined as an axle, the peptide bond, rotating about the bases of two cones, as shown in FIG. 9. Because the error surface (i.e. backbone error as a function of angle of rotation of $C_{i-1}$) was found to be smooth, with one or two local minima at most, a binary search (on rotation angle γ in FIG. 9 ) was used to find the absolute minimum rather than trying, for example, all possible angles in increments of ten or so degrees (26). 360 tests would be required to find the best angle with 1° accuracy stepping one degree at a time, as opposed to about 15 with the present technique. This search process is effectively a local energy minimization on the two peptide atoms with one degree-of-freedom.

Figure 10:
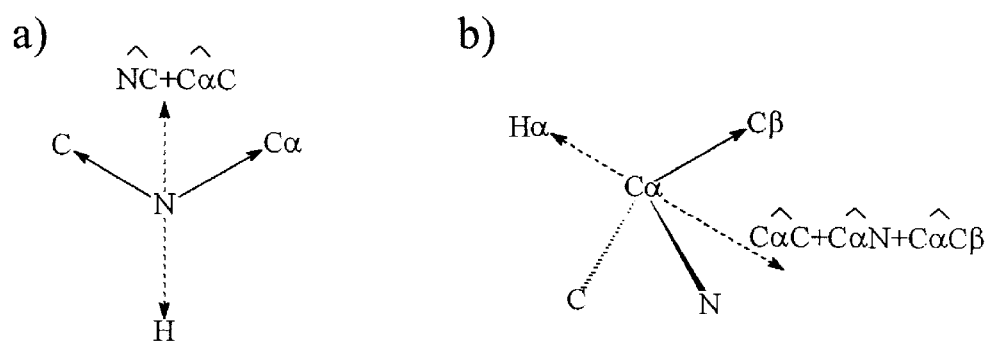
FIG. 10 shows the calculation of the a) H and b) Hα co-ordinates by taking the direction opposite the sum of the unit vectors for each of the other atoms attached at the same node, as indicated.

If no solution could be found within a maximum backbone error tolerance (specified by the user), the current step was aborted and the program would back up one residue, choosing new random co-ordinates to try. If a "good" solution was found, O was then placed using the planarity of the peptide bond, virtual bond angle $\angle O_i$—$C\alpha_i$—$C\alpha_{i+1}$ and length O—Cα (4). The amino hydrogen was calculated only approximately, using a typical N—H bond length (27) and the direction opposite the sum of unit vectors in the directions N—C and N—Cα. Similarly, Hα was approximated in the direction opposite the sum of Cα—Cβ, Cα—N and Cα—C (FIG. 10). Additional atoms appearing at the N- and C-termini were appended in a similar fashion.

Placement of Sidechains—Static Rotamer Dictionary

The last part of protein construction is the addition of the sidechains. In the method, the complete backbone is in place at the time when the sidechain is to be added. Methods for sidechain placement on protein backbones have been published, for example using backbone-dependent rotamer dictionaries such as that used by SCWRL, or by self-consistent ensemble optimization (Lee C, Subbiah S., J.Mol. Biol. 1991;217:373–388, and Lee C., J.Mol.Biol. 1994;236:918–939) which optimizes a large collection of sidechain conformations simultaneously, iteratively, beginning with an initial guess.

Functions were written to generate amino acid sidechains based on standard atom and bond parameters, and a pre-computed set of standard rotamers—a static rotamer dictionary was generated. Rotamers are built using all sidechain atoms, including hydrogens, as well as the backbone N, Cα and C. These latter three atoms allow for a canonical alignment of the sidechains into a rotamer dictionary to allow for easier placement later on. The static rotamers were constructed using discrete $\chi$ angles, varying in quantity and value with residue type. Hydrogens are typically added on equally spaced, in the staggered conformation where applicable.

A randomly-selected standard rotamer was attached to the growing backbone once the β-carbon position and backbone N and C are determined at that residue. This process should remove the need to perform detailed calculations at each residue to determine the positions of sidechain atoms. This is expected to be efficient, using a sort of look-up table, and requiring only a simple rotation and translation for each atom from the dictionary co-ordinate frame.

Placement of Sidechains—Backbone Dependent Rotamers

Using the same rotamer generation techniques used to make the static library, rotamers could also be computed and placed on-the-fly, atom by atom, with arbitrary $\chi$ angles. This was done together with a sampling approach. The backbone dependent rotamer library/database of Dunbrack et al (Dunbrack R L J, et al., J.Mol.Biol. 1993;230:543–574, and Dunbrack R L J, Cohen F E. Protein Sci. 1997;6:1661–1681) is derived through a statistical analysis of protein sidechain rotamers. This was used as a sampling distribution function for the placement of rotamers on-the-fly. Once the location of Cα, N and C at a given residue are known, along with the direction of Cβ, the remainder of the sidechain can be completely defined by up to four dihedral angles ($\chi 1$, $\chi 2$, $\chi 3$, $\chi 4$) (excluding hydrogens). First the $\phi$ and $\psi$ values at the residue are computed, and used along with amino acid type to index into the backbone-dependent rotamer database, which is discretized at every 10°×10° region of Ramachandran space. This database provides a series of rotamers, expressed as $\chi$ angles, each with an associated probability. The sum of probabilities over all rotamers in a given bin is always 1.0, so the database was employed as a discrete probability distribution function for rotamer $\chi$ angles. Hydrogens are placed in most cases simply using standard dihedral angles, such as 180°, −60°, 60° for methyl hydrogens.

Placement of Proline Sidechains

Figure 20:
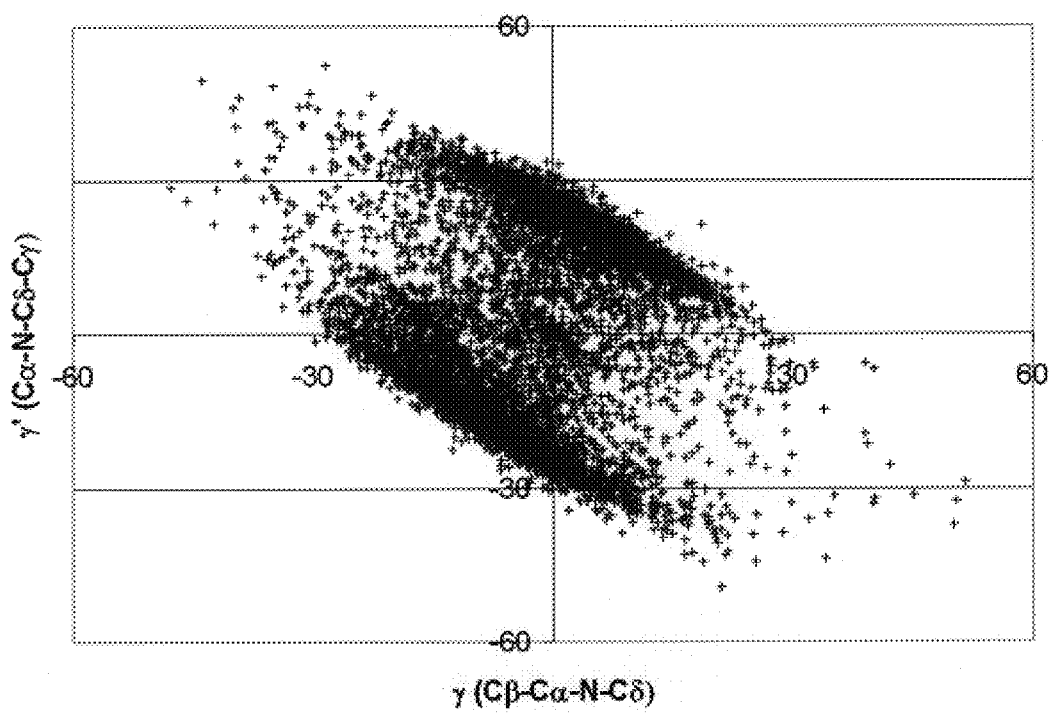
FIG. 20 shows two of the five possible dihedral angles in the proline ring, enough to uniquely determine its conformation, plotted against each other for all Pro residues in the non-redundant set of the PDB. For a given value of one angle, a valid range for the second can be easily picked out as described in Example 2.

For the special case of proline, a completely different construction method was used, as follows. First Cδ is placed using the approximate planarity of proline's imino nitrogen and a standard bond length and angle. The location of Cβ is fixed by the backbone position, so this leaves only Cγ to place. It was found empirically that given γ=dihedral(Cβ—Cα—N—Cδ) (which is now fixed), then $-0.8*\gamma<\gamma'<-0.8*\gamma+32$ or $-0.8*\gamma-48 <\gamma'<-0.8*\gamma-16$, where γ'=dihedral(Cα—N—Cδ—Cγ) (see FIG. 20). Hence one of these two ranges was chosen, with 50% chance each, for γ', and the optimal value in that range found by a binary search, to minimize errors in bond lengths and interior ring angles. If a total error of more than 12.5 degrees squared was found, the other γ' range would be checked, or backtracking would occur. This method results in good proline models, except that they sometimes have unusual puckering phases (Cremer D, Pople J A, J.Amer.Chem.Soc. 1975;97:1354–1358 and Hooft R W, Vriend G, Sander C, Abola E E. Nature 1996;381:272–272).

Results

Input to the INITTRAJ program takes the form of a simple text or FASTA-formatted file containing the sequence to be folded, using the one-letter amino acid abbreviations. INITTRAJ generates the trajectory distribution database and packages it into the ASN.1 input file used by FOLDTRAJ. The running time of INITTRAJ scales linearly with sequence length and so is simply O(N). Default configuration parameters are read in each time the program is executed as well, overridden by parameters passed in an optional configuration file.

The values of the parameters will affect both the speed of the program, and the resulting standard deviations in bond angles, lengths and improper dihedrals in the structure. These parameters include the average number of tries to place the (i+1)th residue before backtracking, the maximum squared error tolerance permitted without rejecting a solution for the backbone atoms as poor, and a parameter for "atom bounciness" with zero corresponding to hard atoms and positive values soft atoms. Increasing the error tolerance will speed up the program but generate poorer structures, evenly distributed over all of Ramachandran space. Decreasing the error tolerance may prevent any structure from being found, and will result in an unrealistically "perfect" protein. A value intermediate to these extremes, 50 degrees squared cutoff, was used. A value of 100 retries on average before backtracking at each residue was chosen, generating structures quickly while rarely backtracking more than 2–3 residues at a time. For soft atom collisions, an "atom bounciness" of 0.25 was used as a very crude approximation to a Lennard-Jones type potential function.

As the method proceeds, coordinate values are added to the chemical graph data structure. Output from the program is a protein structure in NCBI's MMDB ASN.1 format, or a PDB file. In testing, the method works with even the largest of eukaryotic proteins, for example a random conformer of BRCA2 (>3000 amino acids) completes in about an hour and uses only 40MB of RAM on a 400 MHz Pentium II processor running the Linux operating system.

Testing With Myoglobin

To see more clearly the effect of collision testing and optimizing backbone angles, the database sequence 1llM (sperm whale myoglobin, 154 amino acids) was randomly generated 250 times.

With checking for hard-sphere collisions only between Cαs and no backbone atom optimization, each run took an average of 2 seconds (on a Pentium II-300) with an average of 179 tries per run, where a "try" is defined as an attempt to place an amino acid, whether successful or not. In this case, the only way a placement could fail was by Cα collision. The mean radius of gyration ($R_{gyr}$) was 27.3±6.2 Å (compared to 15.19 Å in the folded holo-protein) and end-to-end distance ($R_{NC}$) was 66±26 Å (19.45 Å in the native holo-protein). With complete collision testing and backbone checking, each protein took an average of 155 seconds, or about 51000 tries, and resulted in a radius of gyration of 52.0±11.1 Å and end-to-end distance of 123±47 Å. A histogram of $R_{gyr}$ in both cases (FIG. 12) shows a narrow spread, skewed to the right for the Cα-only walk, and a broader right-skewed shape for the all-atom walk. As expected collision testing and backbone optimization swell the protein to roughly double its size when non-Cα atoms are placed arbitrarily (or equivalently, atoms are assumed to have zero radius except Cα, which was given a diameter of 3.81 Å, the distance between consecutive Cαs). Also, many more tries are required until valid atom placements can be found. Steric hindrance greatly reduces the area of conformational space open to the protein.

Further tests with myoglobin were used to compare the effects of other parameters on the performance of the method, with results summarized in Table III. From this it can be seen, for example, that the use of soft atoms, as opposed to hard atoms, reduces the average time by about 40 seconds, results in many less crashes and backbone errors occurring, and produces significantly more compact structures, as may be expected. The use of flat rather than amino-acid based trajectory distributions slows down the execution time a little since more time is wasted trying to place atoms in invalid locations, but in the end results in structures of similar compactness, except when combined with variable backtracking in which case they are found to be slightly more compact. Other effects are discussed in the following sections.

Rotamer Placement

Two different methods were used for the placement of sidechain rotamers. The first method involved picking a set of rotamer coordinates for the sidechain from a pre-computed set of static rotamers, selected at random in a backbone-independent manner. This method is expected to be more efficient. The second method involved sampling rotamer angle values from Dunbrack's backbone-dependent rotamer library (Dunbrack and Cohen, Protein Sci. 1997, 6:1661–1681), then using these χ angles to generate the selected rotamer on-the-fly. Testing showed that the latter method was similar in speed, only 4 seconds slower on average, and produced slightly more compact structures (p<0.05), for the myoglobin structure population test (Table III). It was superior in the quality of sidechain placement, as determined by WHAT_CHECK (WHATIF, version 19970704–1848) (Hooft R W, et al, Nature 1996;381:272–272). While the latter method may involve slightly more floating point computations, the time complexity was equalized primarily because the backbone-dependence information biases sampling to avoid obvious backbone-sidechain clashes. The static rotamer placement method ended up discarding many rotamers that clashed with the backbone, apparently because there was no information in that method that prevented the placement of a rotamer that clashed with the backbone. The on-the-fly placement method is of course far more powerful than using a static library, allowing placement of rotamers in arbitrary conformations to allow for better packing when trying to construct compact, folded structures.

Backtracking

Backtracking in a build-up method adds yet another dimension to the time complexity of the algorithm. The setting of 100 attempts was used to place a residue before backtracking, which seemed to work well in most cases. However, in some topologies, a combinatorial problem can arise if the only recourse for the build-up method is to backtrack many residues (e.g. backtracking N residues could require up to $100^N$ failed placements). The kind of topology that causes this problem is a region of low conformational freedom (e.g. a helix) building up along a tube or channel with a dead-end, not uncommon in a folded structure. The only way out is to backtrack to the most recent turn.

Backtracking one step only allows resampling of the same trajectory distribution. If that trajectory distribution is shallow (e.g. Gly), chances are a very different residue placement will be obtained, but if the trajectory distribution is deep and spiked (e.g. Lys), the same amino acid placement can be sampled again and again. This information, the depth of the trajectory distribution, was used to adjust the number of backtracking attempts at each residue. Specifically, the following formula seemed to work well empirically for expressing the amount of "information" in the trajectory distribution:

$$i(t)=400*(6\,\Phi_t(0)+2\Phi_t(5)-\Phi_t(10)-3\,\Phi_t(15)) \quad (2)$$

where i(t) is the number of tries to make at a given residue with trajectory distribution t before backtracking, and $\Phi_t(x)$ is the fraction of trajectory distribution space t which lies above x% of the peak value. For example, $\Phi_t(100)=0$ always, since nothing lies above the peak, and $\Phi_t(0)$ gives the fraction of t which is non-zero. If Eq. 2 results in a value outside the range 4–250 it is truncated to the appropriate boundary value, to ensure the i(t) stays reasonable regardless of trajectory distribution complexity. For sharply peaked distributions, Eq. 2 results in an i(t) close to zero, meaning minimal tries should be made at that residue, while for broader distributions with "hills and valleys", larger numbers on the order of 100 result. This change was successful at speeding up the overall algorithm (Table III), and afforded a speed-up of 28 seconds to the mean times of computation for a random myoglobin with no change in $R_{gyr}$. This kind of "smart backtracking" avoids futile residue placements without affecting the characteristics of the structure.

Trajectory Distributions from Database Frequencies

A trajectory distribution grid size of 400×400 provides 0.9° resolution in θ and resolution in φ between 0.29° (near the equator) and 4.1° (near the poles, but 0.5° when φ>16°, as is the case in all real proteins). Changing the grid resolution of the trajectory distributions affects speed and memory usage of the program. The grid resolution must be fine enough to provide the desired angular resolution between consecutive Cαs.

The "trajectory" from one α-carbon to the next completely determines secondary structure, and it was found that helices corresponded approximately to θ=51°, φ=90° while β-sheets had θ=−165°, φ=60°. This compares well with Gregoret and Cohen (24) who found θ=50°, φ=88° for helix and θ=−160°, φ=60° for sheet. The improvement in implementation comes from choosing from a non-uniform, discrete PDF in cosφ−θ space. The selection of conformations is biased at each residue, without introducing significant biases due to the curvature of the spherical surface.

Quality Validation

Sequences from actual proteins of various folds and lengths under 250 residues were generated, with co-ordinates being calculated for all atoms, and the resulting structures submitted to WHAT_CHECK for analysis. All test proteins passed the nomenclature, chirality/planarity, improper dihedral, peptide bond planarity, carbonyl O placement, bond length and bond angle tests. This confirms that the co-ordinates of the protein atoms are physically and chemically valid, aside from proline occasionally having an unusual puckering phase (Cremer D, Pople J A.

J.Amer.Chem.Soc. 1975;97:1354–1358). The number of interatomic clashes (using the hard atom model) was not significantly larger than that for any crystal structure, the majority occurring between the carbonyl O of one residue and the carbonyl C of the next, and due to the difference in the choice of Van der Waals radii from that of WHAT_CHECK. Packing tests were not very good, as would be expected for a random protein conformer. Many buried unsatisfied hydrogen bond donors were located as well, which is not surprising since only steric clashes have been considered to this point.

Secondary Structure Content

The biases introduced by the use of amino-acid based trajectory distributions were investigated by quantifying amounts of secondary structure in the generated random structures. To this end, 1000 structures were generated for each of 1SEM (an all-β SH3 domain), 2HPR (phosphocarrier protein, an α/β open sandwich) and 1RTP (all α,α-parvalbumin), using both amino acid-based trajectory distributions and unform (equiprobable) distributions. DSSP (Kabsch W, Sander C. Biopolymers 1983;22:2577–2637) was used to detect helical content (at least four consecutive residues with at least one hydrogen bond) but is not capable of detecting extended structure per se. Hydrogen bonded parallel and anti-parallel sheets were virtually non-existent (<0.1% according to DSSP) due to the lack of tight tertiary structure in most of the random structures, so β-strand was detected simply by looking for windows of five consecutive α-carbons spanning 13.25 Å or more.

Figure 21:
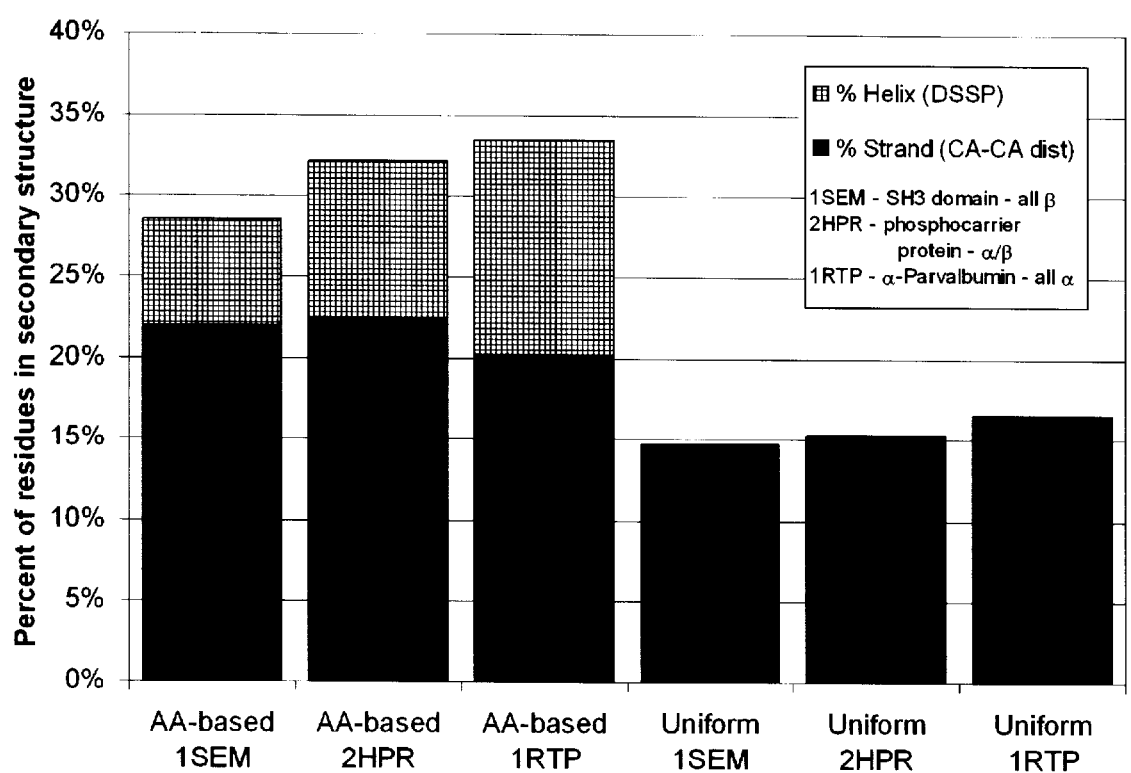
FIG. 21 shows the average secondary structure content in 1000 random conformers of the proteins 1SEM, 2HPR and 1RTP generated using both uniform (i.e. flat) trajectory distributions and AA-based ones (as indicated). Helices were all four or greater residues, and identified with DSSP, while β-strand was identified as any stretch of five or more α-carbons in which the separation from $C\alpha_i$ to $C\alpha_{i+4}$ was greater than 13.25 Å for all possible (i,i+4) windows in the interval. This cutoff was chosen to agree well with PDB secondary structure assignments for real proteins with significant β-sheet content.

The secondary structure content is shown in FIG. 21, which shows that the main effect of the amino acid-based bias is to add helix to the structures, with the largest amount (13.3% helix, 20.1% extended) in the natively helical protein (1RTP) and the least (6.6% helix, 22.0% extended) in the SH3 domain (1SEM). The mixed structure (2HPR) was intermediate to these two (9.8% helix, 22.3% extended). Helices are essentially non-existent when uniform trajectory distributions are used (<0.2% in each case). An increase in the amount of strand produced is evident as well for the amino-acid based structures. 1SEM, 2HPR and 1RTP generated from uniform trajectory distributions had 14.6%, 15.1% and 16.4% extended structure respectively.

Complexity of the Algorithm

Figure 13A:
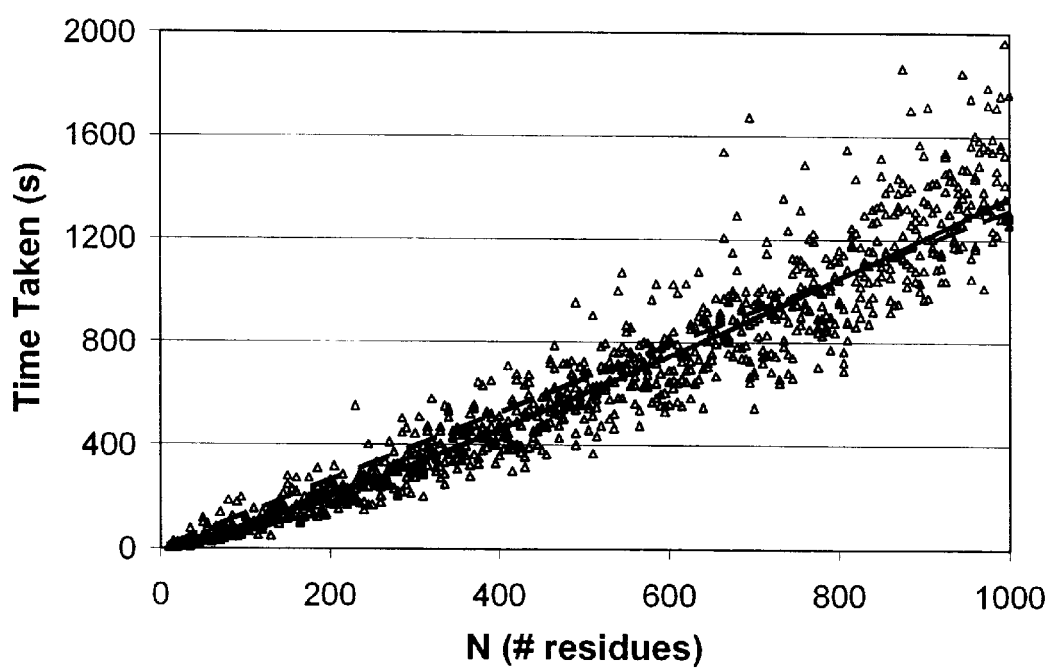
FIG. 13 shows the time taken to generate a series of 995 random structures as a function of sequence length, N (FIG. 13A) and NlogN (FIG. 13B). Each triangle corresponds to a single randomly generated protein and the dark solid line is the line of best fit, in each case of the form $t=aN^b$ with a and b the adjustable parameters. The dark dashed line in (FIG. 13A) is a linear best fit, whereas in (FIG. 13B) the solid line of best fit is already linear.
Figure 13B:
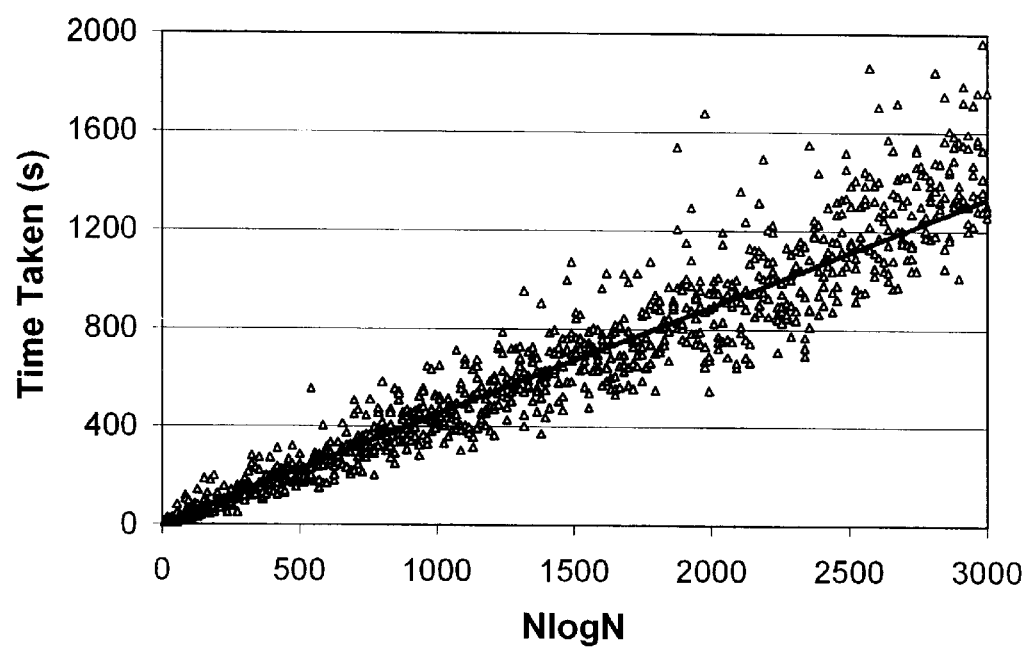

Random sequences with lengths varying from 10 to 1000 amino acids, in increments of 5, were generated to estimate the time complexity of the algorithm used for constructing random proteins. Amino-acid based trajectory distributions were used, along with the hard atom model, a fixed backtracking count of 100 tries and static rotamer placement. Five sequences of each length were created as follows. A count was made of the frequency of amino acid occurrence in the entire *E. coli* genome (a "typical" assortment of proteins) (A: 9.49%; C: 1.17%; D: 5.14%; E: 5.74%; F: 3.90%; G: 7.37%; H: 2.27%; I: 6.00%; K: 4.41%; L: 10.64%; M: 2.85%; N: 3.95%; P: 4.43%; Q: 4.43%; R: 5.54%; S: 5.82%; T: 5.41%; V: 7.06%; W: 1.53%; Y: 2.85%), and for each sequence, each amino acid was chosen randomly according to this distribution. The overall distribution of residues in the resulting 995 proteins was then calculated (in much the same way as it was for *E. coli*) and the composition of each residue was within 0.1% of that in the sampling distribution. The time taken to generate each structure, $R_{gyr}$ and $R_{NC}$ (the N to C terminus separation) were all recorded as well. Time taken was then plotted against both N and NlogN (FIGS. 13A and 13B), where N is the sequence length in residues, and was fitted to an expression of the form $y=ax^b$, with t in seconds on the y axis and N or NlogN on the x axis. In the former case, a=0.38, b=1.18 gave the best fit ($R^2=0.95$), while in the latter, a=0.49, b=0.99 did ($R^2=0.95$). This indicates that the overall structure generation is O(NlogN) and more specifically, to generate a random protein of length N will take approximately $0.49Nlog_{10}N$ seconds on a PentiumII-300 running Linux. Very similar results were observed on a Silicon Graphics Origin 200 system using a single 180 MHz R10000 CPU.

The number of tries, T, was plotted against N where a try was defined as placement of an α-carbon, regardless of whether that placement was removed later on as the algorithm backed up, or was kept for the final structure. The resulting fit to $T=aN^b$ gave a=530, b=0.90 ($R^2=0.99$) indicating that roughly 530 tries were made before placement of each residue was successful. Since backtracking in the random walk occurs after 100 failed attempts to move forward, this also indicates that on average, about five different $C\alpha_{i-1}$ placements had to be tried at each residue before a solution for the backbone co-ordinates between it and $C\alpha_i$ could be found (i.e. a solution with no clashes, and valid angles). The large number of failed tries occurs due to collisions with existing residues (about 25–30%) and due to the lack of a solution for the peptide atoms within the desired backbone tolerance level (about 70–75%).

Figure 14:
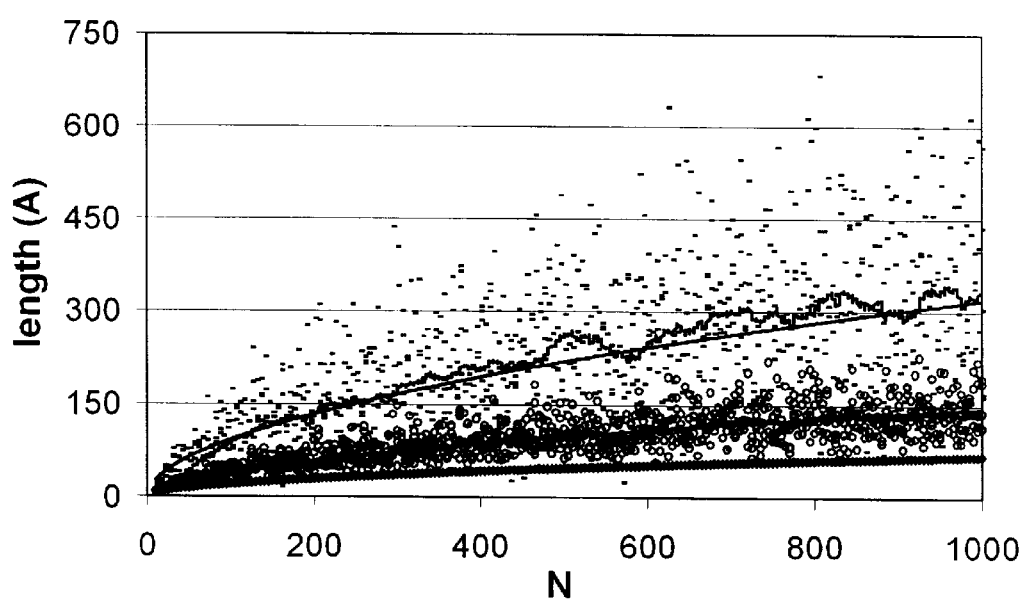
FIG. 14 shows plots of radius of gyration (o) and end-to-end distance (–) against protein length for the same 995 structures in FIGS. 13A and 13B. A moving average for each (window size 50) is shown as a solid, jagged curve, along with the curve of best fit (smooth solid curve). The thick line below all the points is the theoretical minimum radius of gyration, $2.106N^{1/2}$ (See Example 2 discussion).

$R_{gyr}$ and $R_{NC}$ were also plotted vs. N (see FIG. 14). The radius of gyration was found to fit well to $2.84N^{0.57}$ ($R^2=0.82$). Similarly, $R_{NC}$ fit well to $7.72N^{0.54}$ ($R^2=0.54$). The mean value of $C_n/R_n$, characteristic ratio and radius of gyration ratio, $C_n=R_{NC}/Nl^2$ and $R_n=R_{gyr}/Nl^2$ respectively, was found to be 6.03, close to the theoretical value of 6.0 for larger polymers (32).

The amount of memory required by the program is independent of the length of the protein, requiring approximately 40 MB. This allows nearly any modern PC to handle proteins of arbitrary length.

Reconstruction of PDB Structures

If the present algorithm is successful in reconstructing known proteins, then the random proteins it generated would also most likely be valid, possible structures for given sequences. In order to test the ability of the algorithm described above to reconstruct the backbone atoms (namely C, N, Cβ and O), several known proteins were reconstructed by recording their "trajectory graphs" from the following PDB files: 1IIM, 1OMD, 1SEM, 3TS1, 4PTI, 2PCY, 2MHR, 2LYM and 1TIM. This is equivalent to recording the Cα co-ordinates except without Cα—Cα distances; only the direction from each to the next is known. All atom positions were generated completely randomly as before, the only change being that the trajectory graphs used became delta functions, with their peaks at the precise orientation of a given residue in the crystal or NMR structure. No reconstruction took over one minute, and most less than 10 seconds.

Structures were generated with a backtracking retry value of 10 rather than 100, since very little could change between these retries. Also, bump checking was turned off since side chains were being placed (but not used in calculations) and were expected to collide since they were being placed randomly. Bump checking was not expected to improve the quality of the backbone since the whole shape of the protein was approximately held rigid, so some backbone-backbone clashes occurred. The simplifications the algorithm makes, namely constant NCα and CCα bond lengths, etc. would not allow certain residue backbones in real proteins to be reconstructed without backbone-backbone clashes.

Depending on the structure, the backbone error tolerance had to be increased to various levels to allow each protein to be built. Usually one or two residues per structure required relatively large errors in some of their angles in order to find any valid solution at that residue. This was most often due to an incorrect Cβ placement at that point. These occurred at turns coming out of helices or sheets and leading into new ones. Some of the proteins were chosen with different types of ligands attached (the heme ring in 111M, calcium bound to 1OMD, tyrosinyl-5'-adenylate in 3TS1 and a small peptide in 1SEM) to observe the quality of reconstruction in such instances. Some of the observed Cβ distortions occur at or near the sites of ligand attachment since liganding can alter residue conformation. A slightly better structure may have been obtained if different tolerances were used at different locations, but the "worst case" error was used as the cutoff for all residues.

To compare the reconstructed proteins with their crystal structures, the co-ordinate RMSD of various atoms and atom pairs were determined and summarized in Table IV. There is no obvious relationship between protein length or resolution and quality of the reconstruction. All were fairly well reconstructed, with the worst case being 2PCY, having poor N and C placement. This is at least partially due to the fact that every ten or so residues, a Cβ is very poorly placed (>0.5 Å in space away) in the structure. The latter five proteins were reconstructed by Rey and Skolnick (4) using their algorithm and their final values for Cβ, C, N and O RMSDs are shown as well for comparison.

The square root of the backbone tolerance mentioned earlier is the cutoff of the backbone error for each residue, and is shown in Table IV. Also shown is the resulting average backbone error for the reconstructed protein, and that for the PDB structure. These latter values can be thought of as an angular backbone RMS error (RMSbb error) of the recorded structure from a structure with "ideal" bond lengths and bond angles at each residue, even if such angles could not all simultaneously exist in space. This should not be confused with atomic co-ordinate RMSD.

Generally, the closer the reconstructed RMSbb error was to the crystal structure RMSbb error, the better the reconstruction. Note that in all cases, the reconstructed RMSbb error was significantly less than the cutoff, indicating that only a few residues actually exhibited deviations as large as this cutoff value and most were much smaller.

Figure 15A:
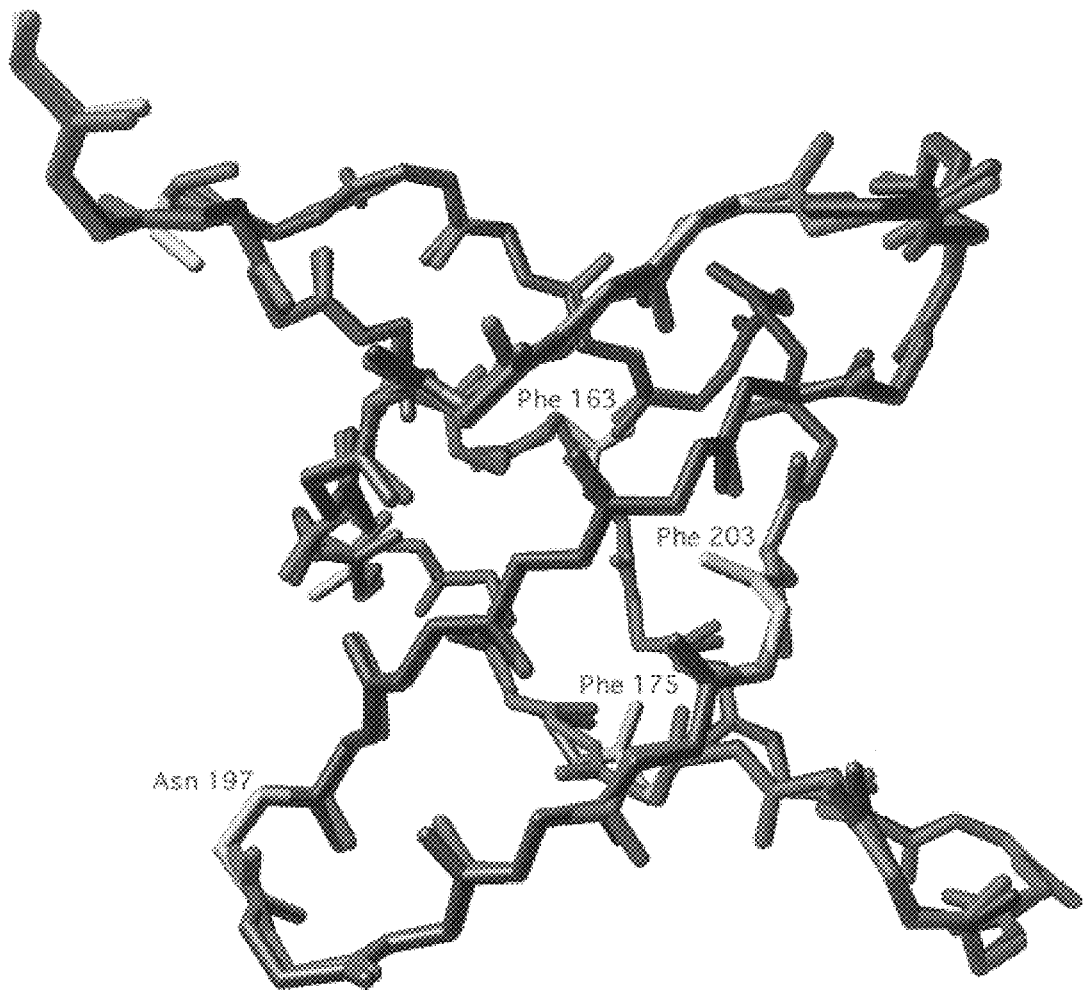
FIG. 15 shows reconstructions of PDB structures a) 1SEM, an SH3 domain and b) 1OMD, the calcium-binding protein oncomodulin. The crystal structure backbones are shown in red, and the reconstructed ones in blue. Areas in which the reconstruction was particularly poor are highlighted in green, and in some cases, the offending residues labeled. 3-D alignment was obtained solely based on Cα co-ordinates. The reconstructions appear quite good except at a few residues in each protein, either at sharp turns or where ligands are normally attached. A poor Cβ placement (>0.5 Å error) occurs at or adjacent to each labeled residue.

Each reconstructed protein was then run through WHAT_CHECK for analysis. Results were generally poorer than those from de novo generated peptides, due to the added constraints and increased backbone error cutoff (which is normally set to about 7 degrees). Nevertheless, all except 2PCY and 2MHR had normal bond length variability and bond angle variability, despite a few extreme values. In most cases, these occurred at or near locations where a Cβ had been grossly misplaced. Several structures had high improper dihedral variability, usually at or near the same sites where bond angles or lengths were poor. Generally the backbone at 80% or more of the residues was quite good however. Two structures, with areas of poor reconstruction highlighted, are shown in FIG. 15.

Comparison to Experiment

Earlier studies by Haas' group (Amir D, Krausz S, Haas E. Proteins 1992;13:162–173; and Gottfried D S, Haas E. Biochemistry 1992;31:12353–12362), looked at the distance distributions from N-terminus to fluorescently labelled lysine residues of bovine pancreatic trypsin inhibitor (BPTI), using fluorescence resonance energy transfer (FRET). The experiments were done under denaturing and reducing conditions, first in a mixture of guanadine hydrochloride and glycerol at −30° C., and later without the glycerol at 20° C. and 35° C. Their distributions were fit to skewed Gaussian functions, of the form $f(x) \; x^{2}*e^{-a(x-b)^2}$ with x the distance in question and f(x) the frequency of occurrence. To compare, 5000 structures of BPTI were generated using each of the trajectory distribution methods as described above: uniform and amino-acid based. Distances between the α-carbon of the N-terminal residue and the Nζ of the lysine sidechain on each of residues 15, 26, 41 and 46 were recorded, the same places fluorophores were attached in the described experiments. All distance distributions fit well to the skewed Gaussian form, with $R^2 > 0.98$.

The results (Table V) were compared with those found by Haas and co-workers. The agreement is good, when the variation in their own data at different temperatures and different conditions is taken into account. The amino-acid based structures have distances about 4 Å greater than the uniform ones, and although the peak for the (1–46) distance appears much greater (55 Å vs. 45 Å for uniform) the distribution is very flat here, making it difficult to choose an exact peak value. Both methods explore similar amounts of conformational space. The peak values are slightly higher than those found by Gottfried and Haas using a one-component model, though within one standard deviation, except for (1–26). However, they also fit their data to a two-component model, with the greater peaks being 45, 50 or 55, and 45 for (1–26), (1–41) and (1–46) respectively, very close to the peak values obtained here. The full width at half maximum (FWHM) is comparable to Amir et al for (1–15) meaning a similar amount of conformational space is explored, but it is difficult to compare for (1–26) since they only fit the fluorescence lifetime data to a two-component discrete system and not a continuous model. Their data is thus constricted to appear as two distinct sub-populations. The observed distribution appeared more like a single Gaussian with a "hump" on it (not shown), indicative of overlap of two or more Gaussian-like functions. The results indicate a complex superposition of Gaussians for the (1–41) and (1–46) distance distributions, not representable by a simple one- or two-component model. Gottfried and Haas mention that "the model used is not a perfect representation of the real system".

Discussion

Figure 16:
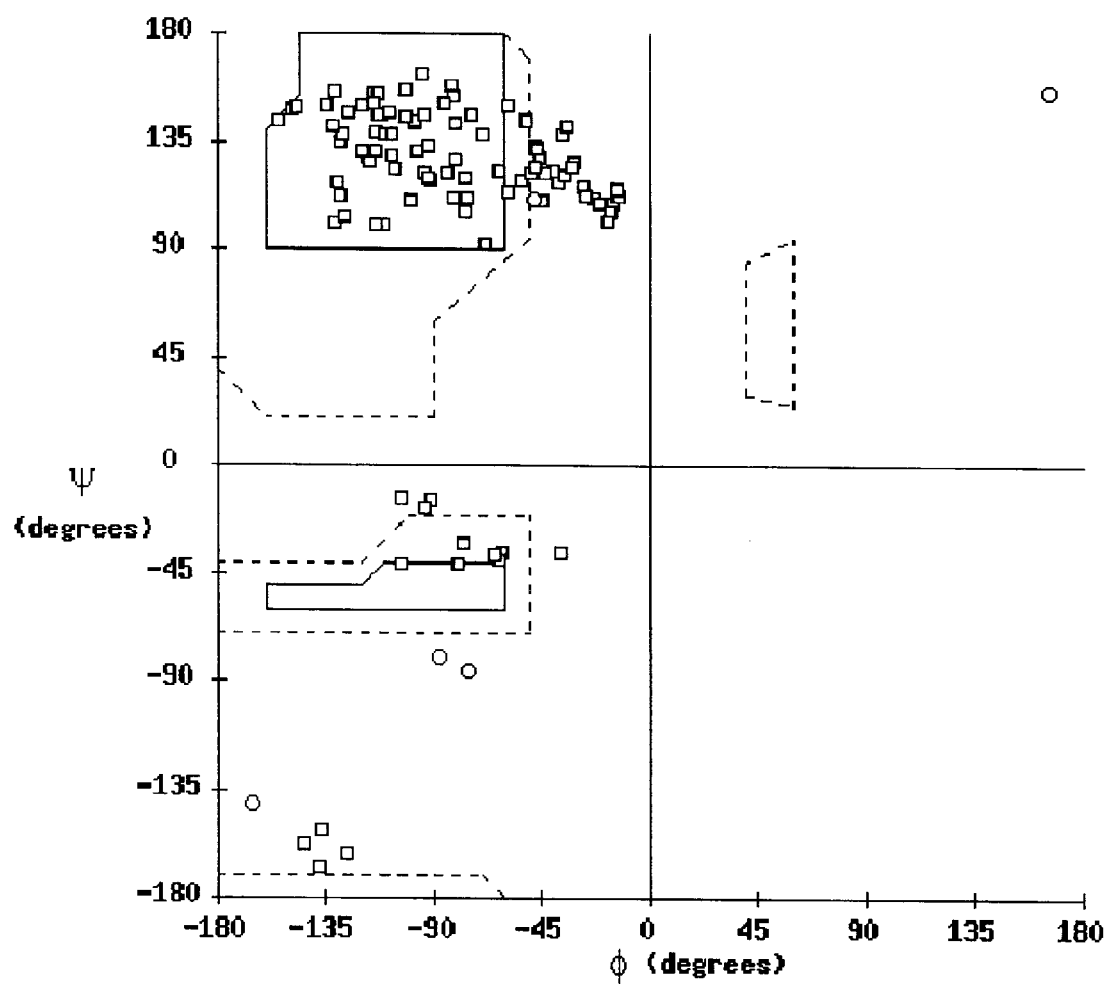
FIG. 16 shows a Ramachandran plot of random 1OMD (oncomodulin) with backbone angle and length constraints and bump checking in place, but using uniform trajectory graphs (i.e. all points on the surface of the sphere are equiprobable to be chosen). Gly residues are indicated as circles while all other residues are squares. Observe that nearly all non-Gly residues fall within the "allowed" regions, despite the fact that no secondary structural bias was included during generation of the structure.
Figure 17A:
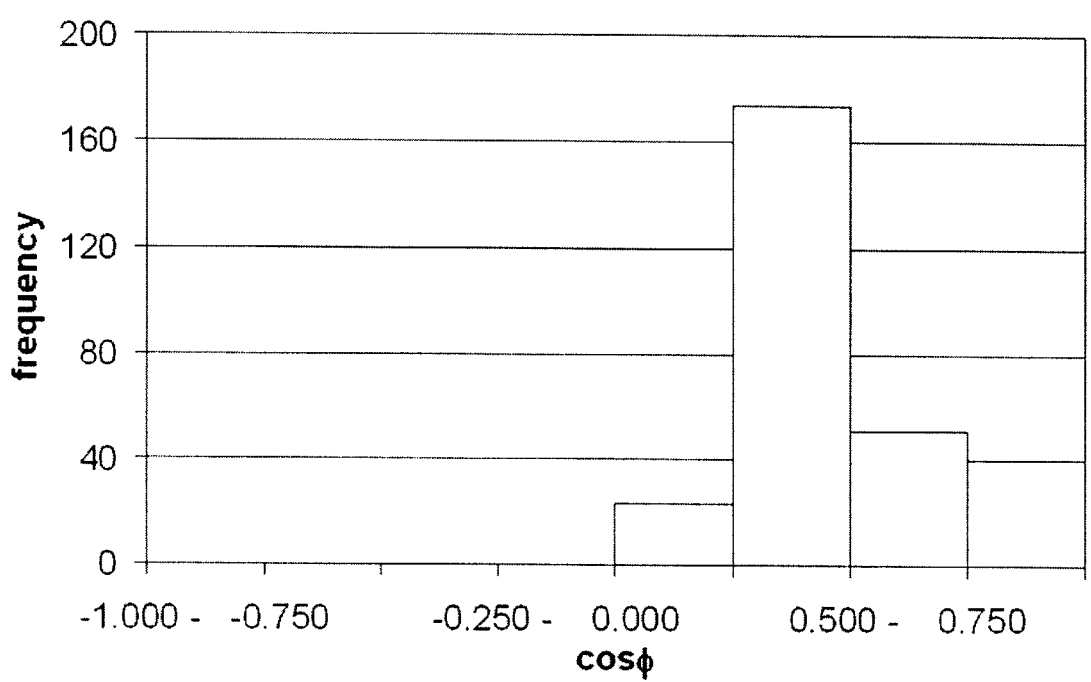
FIG. 17A) and FIG. 17B) show the distribution for Ala of cosφ and θ respectively in the region around Φ=–150°, ψ=90° which is predominantly β-sheet. cosφ is very sharply peaked at about 0.4, while θ has two peaks, one near 25° and another, larger one near –165°.
Figure 17B:
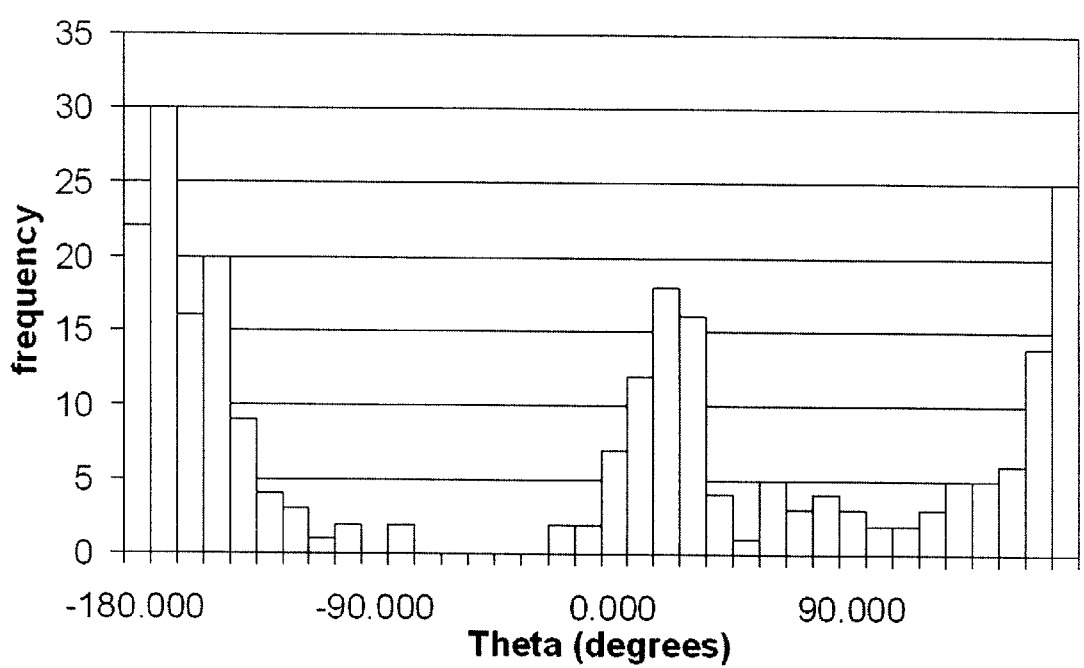
FIG. 17 shows the relation between trajectory space and Ramachandran space.
FIG. 17C) and FIG. 17D) show the area near (Φ=–30°, Ψ=–30°, the α-helical region of Ramachandran space. The cosφ peak has shifted to about 0 and only one sharp peak occurs for θ at about 55°, with a second broad, small peak at –105°. Similar results were observed for other residues (not shown), and each region of Ramachandran space had a unique set of peaks in trajectory space (cosφ-θ space).
Figure 17C:
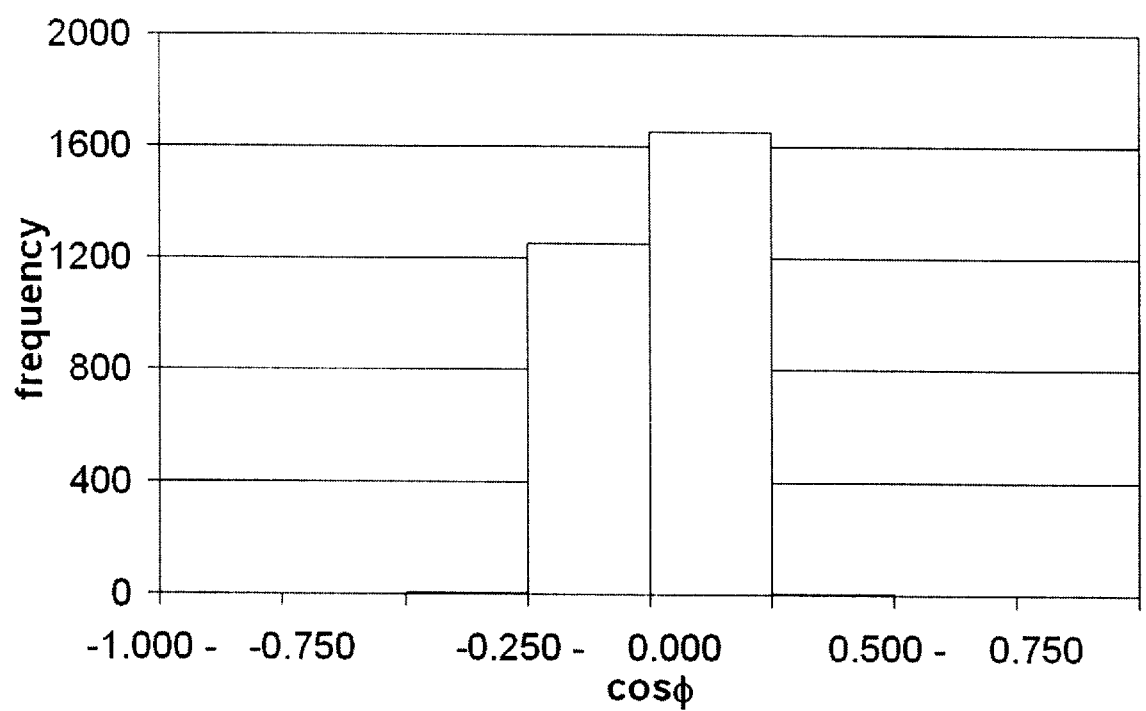
Figure 17D:
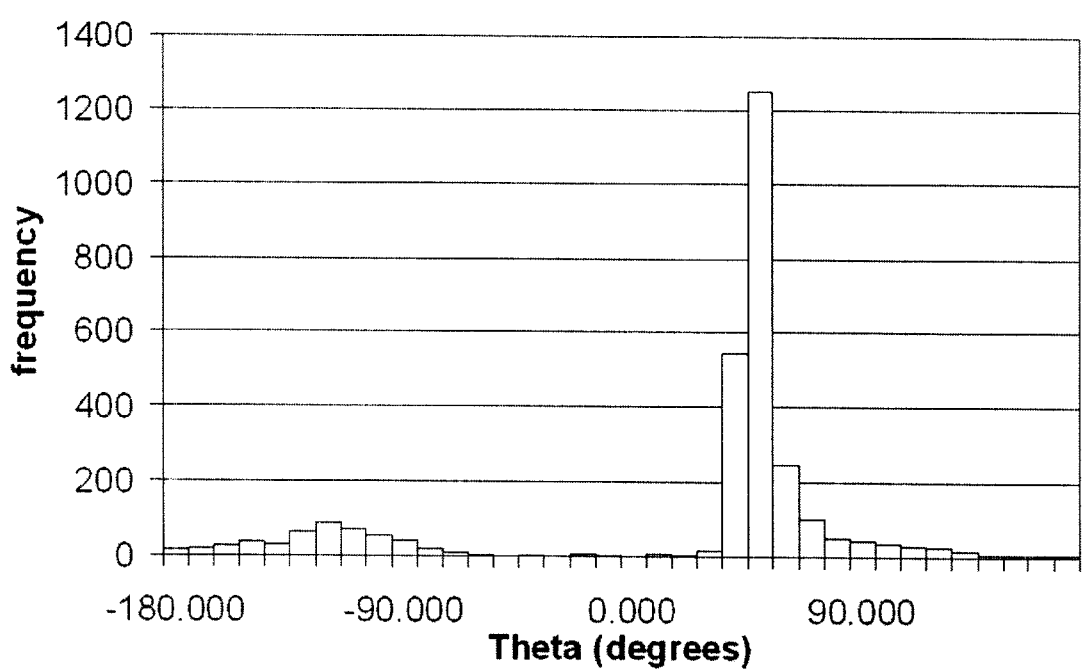

The present method allows sequences of lengths in the thousands to be constructed in under an hour. This is due to the kinetic nature of the random walk, backtracking only when necessary, and otherwise proceeding into space in any and all directions, as well as the binary-d tree used for efficient collision testing. It is interesting to note that by using uniform trajectory graphs, avoiding collisions, and ensuring accurate bond lengths and bond angles, all residues in the resulting randomly generated proteins except Gly fall within the allowable regions of Ramachandran space (FIG. 16)(33). The observed discrimination is a result of steric clashes and possibly Cβ placement (which was used to place C and N) since the lookup table used contains some secondary structure bias. Only certain areas of Φ-Ψ space are populated because the bond length and bond angle restraints, and van der Waals repulsions physically forbid certain conformations of the backbone. It has been known for some time (32) that by simply applying steric restraints, and implicitly fixing bond angles and bond lengths, the acceptable areas of Ramachandran space correspond well to areas of low rotational potential energy.

As the random walk proceeds, the points chosen will have some effect on the conformation of that section of the backbone (i.e. helical, sheet, turn, etc.) and so a relation between trajectory co-ordinates ($\phi$, $\theta$) at a given residue, and those of Ramachandran space, ($\Phi$, $\Psi$) was tested for and confirmed. The relations are complex, but could be expressed empirically in a large transformation table. Generally, in a given region of Ramachandran space, the distribution of $\cos\phi$ (and hence $\phi$) was sharply peaked while $\theta$ had one or two preferred values (FIGS. 17A, 17B, 17C, 17D), which indicates up to two favored locations for $C\alpha_{i+1}$ related by a rotation about the $C\alpha_{i-1}C\alpha_i$ vector. Each point in Ramachandran space corresponded to a very narrow range of values of $\phi$ and $\theta$. Gregoret and Cohen (24) performed a similar random walk, but placing only C$\alpha$s, and dividing up $\phi$, not $\cos\phi$, uniformly. They also found that this space had a direct mapping to Ramachandran space, following from the local excluded volume effects of a polypeptide chain. The existence of such a mapping means that the trajectory graphs implicitly contain information about each residue's preferences for the various forms of secondary structure.

Figure 18A:
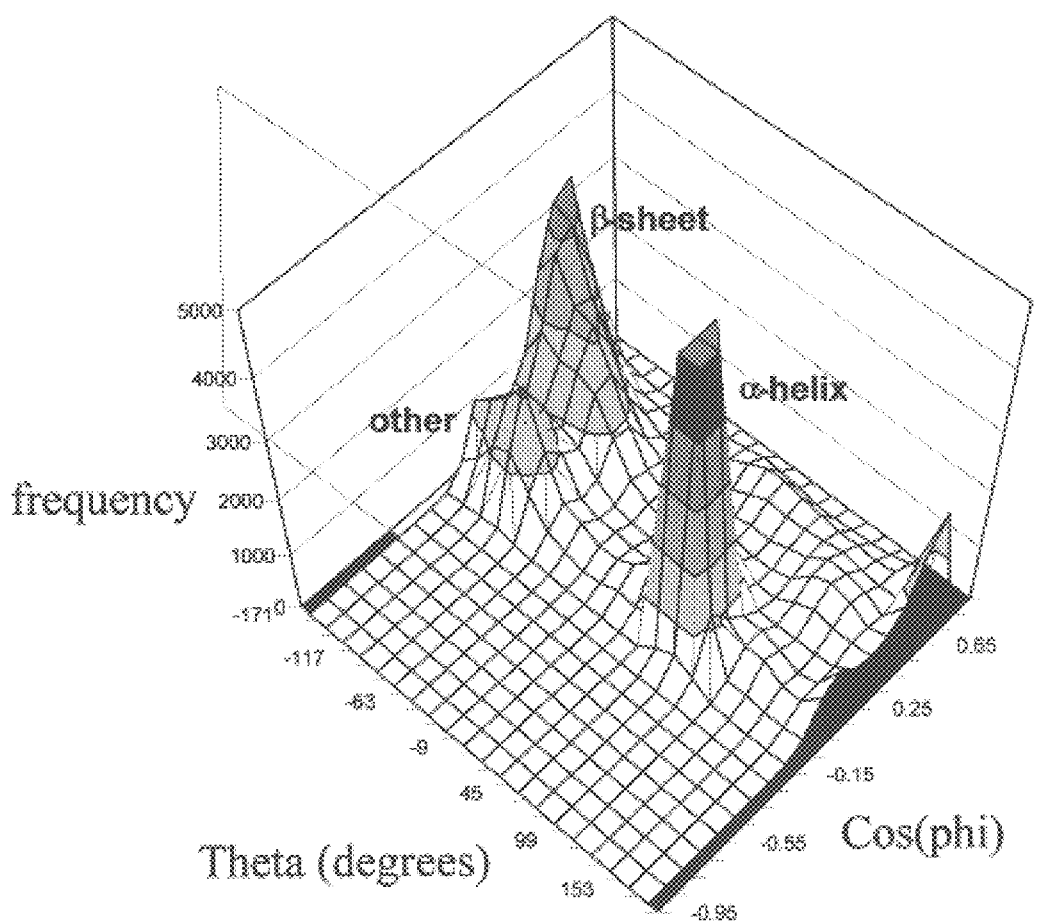
FIG. 18 shows an average trajectory graph or distribution for all residues in all proteins in the non-redundant set used (FIG. 18A) and Ala only (FIG. 18B), plotted in θ-cosφ space. Each grid square corresponds to a patch of equal area on the surface of the sphere (see FIG. 19). The α-helix peak has been truncated for clarity, and note that the graph "wraps around" in the θ dimension. Each peak corresponds to a different type of secondary structure, as labeled, just like in Ramachandran space. Note residues in random coil or turn conformation can actually fall anywhere on the trajectory graph, including on top of the α-helix or β-sheet peaks.

The "trajectory" from one $\alpha$-carbon to the next completely determines secondary structure, and it was found that helices corresponded approximately to $\theta=51°$, $\phi=90°$ while $\beta$-sheets had $\theta=-165°$, $\phi=60°$. This compares well with Gregoret and Cohen (24) who found $\theta=50°$, $\phi=88°$ for helix and $\theta=-160°$, $\phi=60°$ for sheet, and the average trajectory graph for all residues in the database (FIG. 18A) compares well with the one they obtained.

Figure 18B:
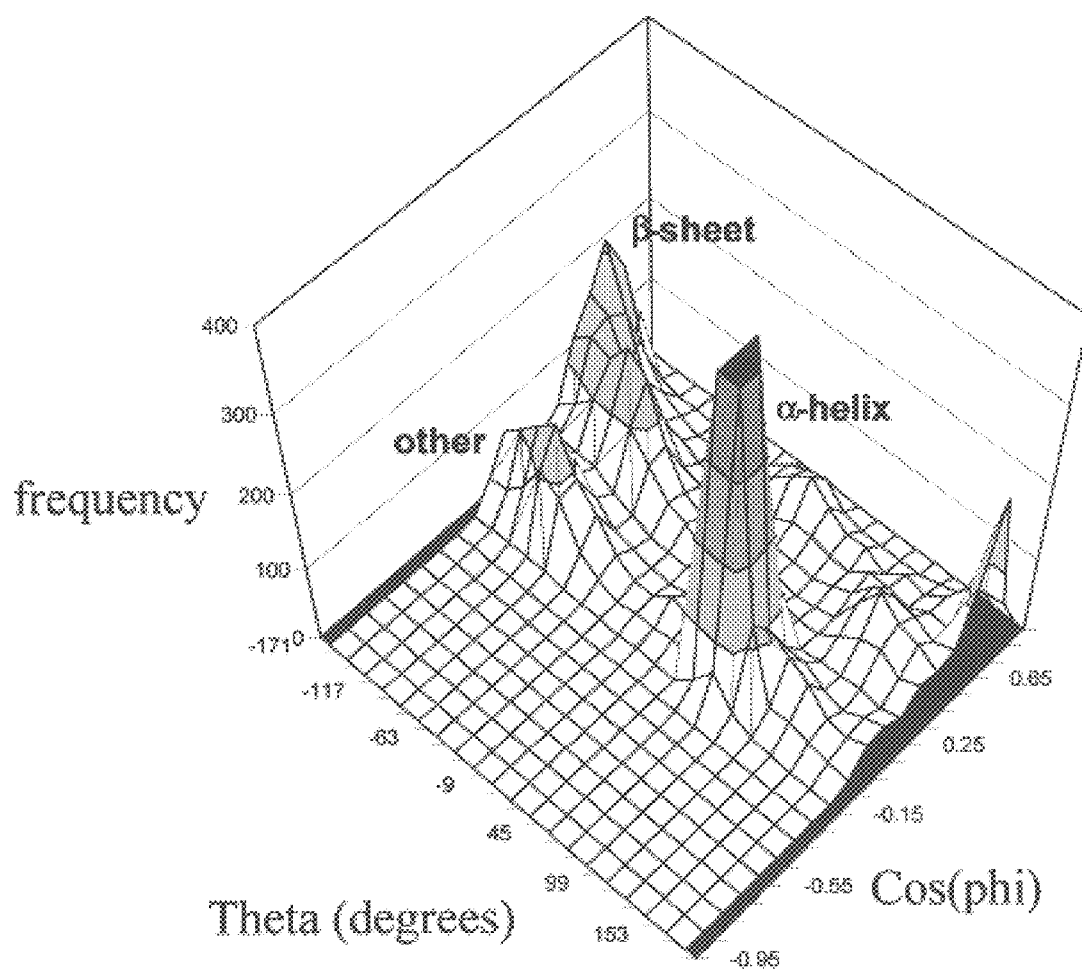

In the present implementation, by choosing from a non-uniform, discrete PDF in $\cos\phi$-$\theta$ space, certain bias has been given to the various types of secondary structure at each residue, without introducing significant biases due to the curvature of the spherical surface. The trajectory graphs as they appear in their native vector space, the surface of a sphere, are shown in FIG. 19, and the representation of these on a flat plane as in FIGS. 18A and 18B can be achieved by projecting these onto the inside of a cylinder, and subsequently unrolling it. It should be noted that there is no easy way to choose N equally distributed points on a sphere, when N is any integer other than the number of vertices found in the five Platonic solids (34). The method employed ensures that the probability that a patch is chosen is proportional to its area.

A method was developed that is able to generate full-atom instantiations of protein structures of arbitrary sequence and length, in O(NlogN) time, owing primarily to the efficient collision-testing provided by the binary-d tree, but also to the binary search methods used in refining the backbone atoms. These structures are for the most part physically and chemically valid, and could represent possible conformations of proteins in the unfolded or denatured state, for example in 8M urea. The proteins were found to agree well with Flory polymer theory, namely that the radius of gyration varied with the square root of length, as did the end to end distance. In contrast to other random walk protein generators, no attempt was made to discretize space on a lattice, and the growing chain was free to wander wherever it would fit. The quality of the protein reconstructions testify to the method's soundness.

Figure 12:
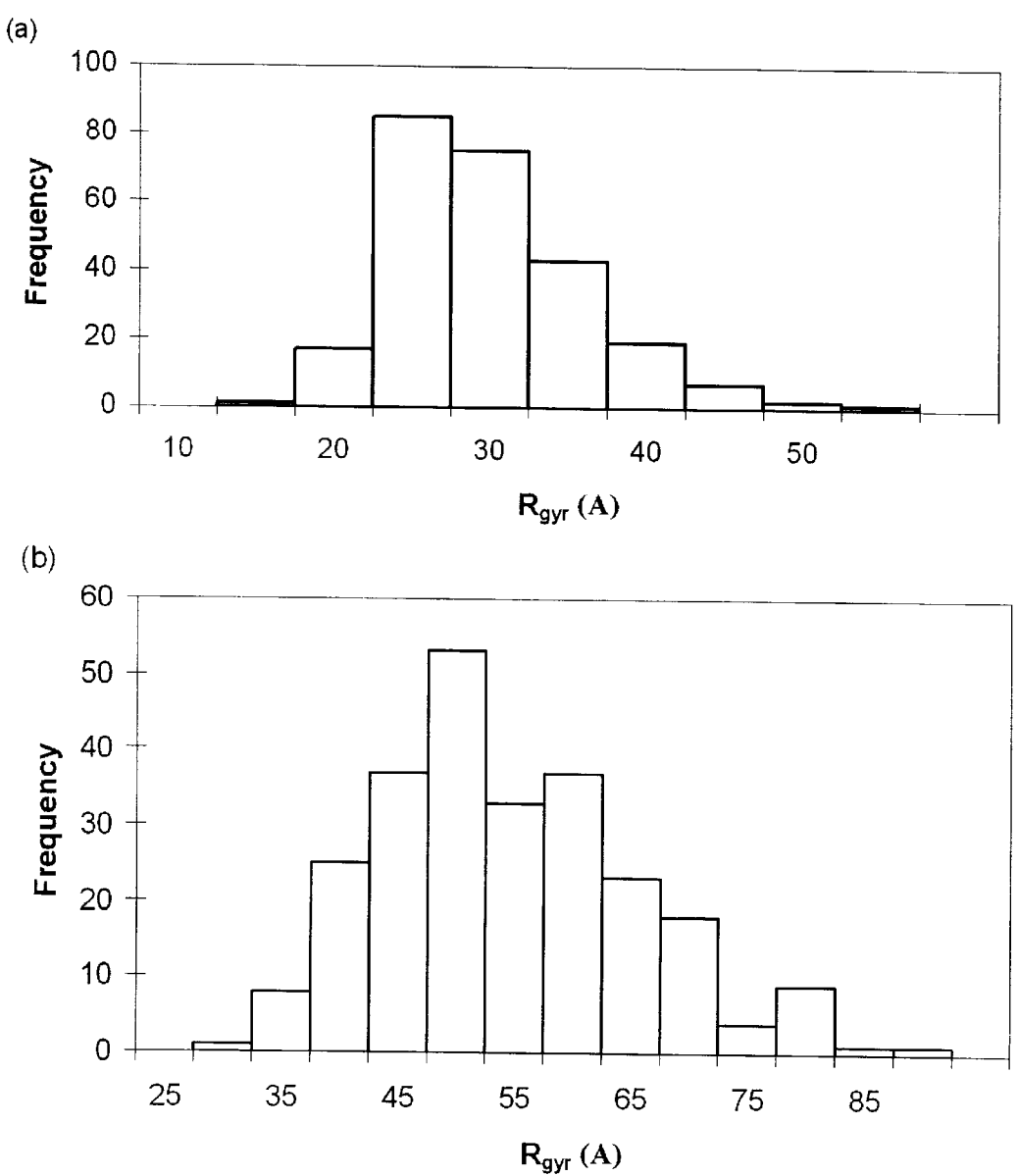
FIG. 12 shows the distribution of radius of gyration (in Å) for 250 randomly generated myoglobin structures, without (a) and with (b) full collision testing and backbone optimization. The distributions appear to be skewed to the right, so that the peak value is slightly less than the mean.

The method has been shown to work well at both ends of the spectrum: reconstruction of known, folded proteins and generation of random, denatured protein structures. A large body of theory on general random walks and polymers (11) has investigated the relationships between polymer length and 3-D shape, and is useful for comparison to these randomly generated structures. For a polymer generated via random walk, with N atoms, bond angle $\theta$ and length l, $$\frac{R_{gyr}^2}{Nl^2} = \frac{1-\cos\theta}{6(1+\cos\theta)} \quad (3)$$

so that for a protein with l=3.81 Å and $\theta\approx107°$, $R_{gyr}^2$=4.419N is expected. However, since a self-avoiding kinetic walk was used in this study, the walk is statistically biased, increasing the expected size. Also, since entire backbones and sidechains are being added on and tested for collisions, rather than just testing for collisions between $\alpha$-carbons, even larger values are expected. Using N=154 this gives an expected $R_{gyr}$ of 26.1 Å for myoglobin. Hence the observed average of 27.3±6.2 Å when non-C$\alpha$ collisions and backbone optimization was ignored agrees with this. The distributions of $R_{gyr}$ shown in FIG. 12 illustrate the swelling of the distribution, as well as the mean, when full bump checking is used compared with the relatively narrow distribution achieved when only C$\alpha$ collisions can take place and all residues are treated as spheres of constant radius. It is also interesting to note that in both cases, $(R_{gyr})^2$=5.86 was close to the expected limit of 6 as N approaches infinity. The theoretical equation for $R_{gyr}$ served as a lower bound for the observed values in the 995 randomly generated proteins as well, as can be seen in FIG. 14. The fitted exponent for the $R_{gyr}$ dependence on N of 0.57 is close to the value of 0.6 predicted by theory for a kinetic self-avoiding walk in 3 dimensions (Pietronero L. Phys.Rev.Lett. 1985;55:2025–2027).

Figure 15B:
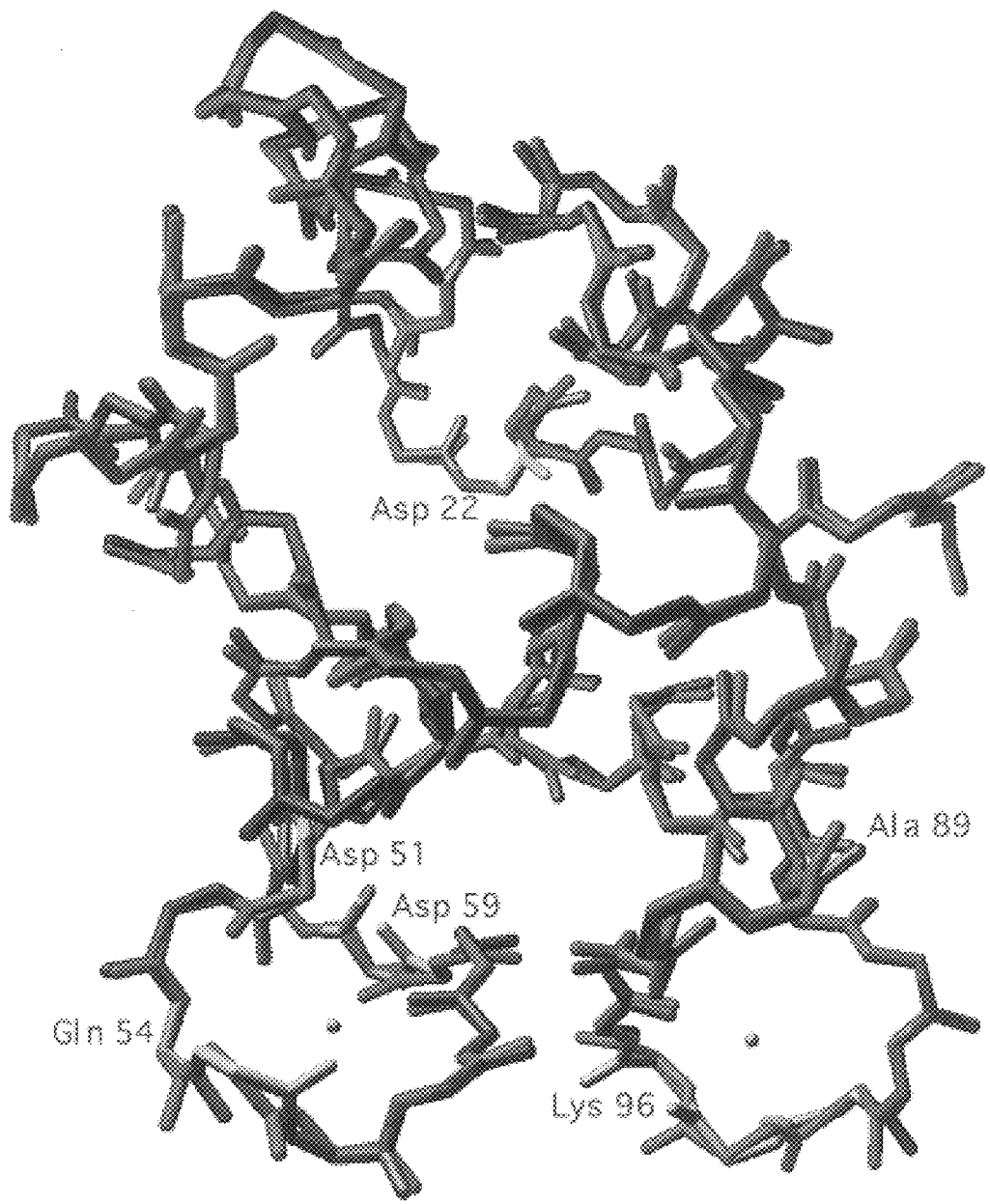

When reconstructing known folded proteins, the placement of C$\beta$, which is the first atom placed after C$\alpha$, is crucial to the calculation of the remaining nearby atoms since various bond angles depend on it. Although the method used is very accurate 90% of the time or so, it seems to fail at certain locations, usually within sharp turns, or at amino acids that interact with non-protein ligands (FIG. 15b). However, when generating random proteins, this will be less of a problem, more likely having the implication that certain types of turns will be forbidden by steric clashes. This may be corrected by allowing the C$\beta$ to "wander" in areas where turns are starting to form, to allow these possibilities to be considered.

When a protein is still unfolded and essentially random, a 200×200 discretization is sufficiently flexible to allow a sampling of many conformations. However, the results show that increased precision is required in later generations as the trajectory graphs get refined and the protein becomes more compact, so that a switch to 400×400 trajectory graphs was made. Alternatively, a random displacement between ±½ units (e.g. ±0.9° for $\theta$) could be added to remove some of the discretization effects, since any value within half a unit will still fall into the same discretization bin, and no co-ordinates will be forbidden to the atom placement then.

There is clearly enough information in the amino-acid based trajectory graphs to spontaneously form properly hydrogen-bonded $\alpha$-helices, and the secondary structure content attained is comparable to that of Gregoret and Cohen (Gregoret L M, Cohen F E. J.Mol.Biol. 1991;219:109–122) for their native-like random walks (they found about 13% in helices and 22% strand, comparable to what was found for AA-based structures in FIG. 21). The intrinsic propensity of the residues in the protein to form helices results in twice as much helix on average in 1RTP, the protein which folds into an all-helical structure, compared with 1SEM, which has no helix in its native state. This observed bias must be a result of the bias towards helix of certain residues in the non-redundant set of proteins used to generate the trajectory distributions. Greater secondary structure content, on the order of that found in native proteins, can be generated by further biasing input trajectory distributions based on secondary structure predictions, such as that of the GOR method (Garnier J, et al,. J.Mol.Biol. 1978;120:97–120 and Garnier J, et al Methods Enzymol. 1996;266:540–553).

All publications, patents and patent applications referred to herein are incorporated by reference in their entirety to the same extent as if each individual publication, patent or patent application was specifically and individually indicated to be incorporated by reference in its entirety.

TABLE 1

Information contained in each trajectory distribution record of the database.

| Field Name | Purpose |
| --- | --- |
| Residue number | Primary search key - index into database |
| Amino acid | One-letter amino acid code |
| Dimension | Size of trajectory distribution in both dimensions, normally 400, each residue can potentially have different resolutions of discretization |
| Endianness | Keeps track of what type of CPU the binary data was generated on to maintain platform independence of the file |
| Compression type | Indicates whether bzip2, RLE, or some other compression method was used on the trajectory distribution data |
| Buffer size* | Size of the compressed trajectory information (needed for decompression) |
| Trajectory distribution data* | Actual compressed binary data |
| Integral* | Total area under the trajectory distribution; units are arbitrary |
| Peak value* | Largest single value in the trajectory distribution - allows comparison of relative sizes of different trajectory distributions |
| First non-zero row** | First row in the trajectory distribution array which contains a non-zero number; the first row is row 1 |
| Number of non-zero rows** | The number of rows from the first non-zero row to the last one; rows of zeroes may appear amongst the non-zero ones, but this counts up to the last row with any non-zero data in it |
| Number of elements <= 0*** | Number of entries in the entire trajectory distribution array which are zero; gives an indication of shallowness |
| Number of elements <= 5% peak*** | Same as above, but includes up to 5% of the peak value |
| Number or elements <= 10% peak*** | Same as above, but includes up to 10% of the peak value |
| Number of elements <= 15% peak*** | Same as above, but includes up to 15% of the peak value |
| Timeout | Number of tries at each residue before backtracking |
| Omega mean | Average peptide dihedral angle between residue i-1 and i |
| Omega standard deviation | Standard deviation to use when choosing omega randomly |
| Cis probability | % probability that the bond between residue i and i + 1 will be cis (0 unless i + 1 is Pro) |
| S-S probability | % probability that residue is involved in a disulfide bridge (0 unless Cys) (for future use) |
| Rotamer info | Unused - possibly for storing favored rotamer index |

*has a corresponding field for when the residue is chosen to be cis, provided Cis probability is not zero. All other fields apply to both sets of trajectory distributions (cis and trans) where appropriate, unless otherwise noted; cis trajectory distributions are used to place residue i + 1 when residue i is a cis-proline
**always applies to trans trajectory distribution only; non-zero rows of cis trajectory distributions are stored explicitly
***always applies to most probable trajectory distribution, i.e. trans unless Cis probability > 0.5

It has been shown that using amino-acid based trajectory distributions, ensembles of structures can be rapidly generated which may serve as a plausible model for the denatured state of the protein. Similar amounts of conformational space are explored in the ensembles as are by denatured BPTI in solution, as evidenced by the similar FWHMs and curve forms obtained.

Trajectory distributions serve as an extremely flexible input for the protein conformer generator, acting as a map of conformational space. This allows for future expansion of the method by simply changing the way in which trajectory distributions are generated. Information about adjacent residues, or even experimental data revealing the conformation of certain residues could easily be applied to bias the trajectory distributions, reducing the conformational space available at certain residues.

Having illustrated and described the principles of the invention in a preferred embodiment, it should be appreciated to those skilled in the art that the invention can be modified in arrangement and detail without departure from such principles. We claim all modifications coming within the scope of the following claims.

TABLE II

Direction cosines for C$\beta$ at residue n-1 when there is a cis peptide bond between residues n − 1 and n. They are relative to the reference frame described by Rey and Skolnick (4). Values are global averages over all 414 cis bonds in the non-redundant set of proteins used in this study. Standard deviations are on the order of 0.1–0.2 depending on frequency of the amino acid prior to a cis bond.

| Residue | cos$\delta$1 | cos$\delta$2 | cos$\delta$3 |
| --- | --- | --- | --- |
| ALA | 0.1595 | 0.9518 | 0.03410 |
| ARG | 0.2739 | 0.9351 | 0.1052 |
| ASN | 0.2285 | 0.9381 | −0.06389 |
| ASP | 0.09837 | 0.9303 | −0.06508 |
| CYS | 0.2181 | 0.9433 | −0.01515 |
| GLN | 0.2697 | 0.9333 | 0.02162 |
| GLU | 0.1843 | 0.9451 | 0.09224 |
| GLY | −0.3340 | 0.1663 | 0.1887 |
| HIS | 0.1298 | 0.9566 | 0.04983 |
| ILE | 0.2001 | 0.8726 | 0.1227 |
| LEU | 0.1266 | 0.9035 | 0.1235 |
| LYS | 0.1661 | 0.9563 | 0.07943 |

TABLE II-continued

Direction cosines for Cβ at residue n-1 when there is a cis peptide bond between residues n − 1 and n. They are relative to the reference frame described by Rey and Skolnick (4). Values are global averages over all 414 cis bonds in the non-redundant set of proteins used in this study. Standard deviations are on the order of 0.1–0.2 depending on frequency of the amino acid prior to a cis bond.

| Residue | cosδ1 | cosδ2 | cosδ3 |
|---|---|---|---|
| MET | 0.1235 | 0.9174 | 0.1855 |
| PHE | 0.1477 | 0.9611 | 0.06610 |
| PRO | −0.01185 | 0.9670 | 0.1570 |
| SER | 0.2224 | 0.9337 | 0.02720 |
| THR | 0.3036 | 0.9305 | 0.05830 |
| TRP | 0.2032 | 0.9384 | 0.006974 |
| TYR | 0.1853 | 0.9596 | 0.07812 |
| VAL | 0.1942 | 0.8873 | 0.09114 |

| AA-based | Variable backtracking | Bbdep. Rotamers | Soft Atoms | Time(s)[a] | Tries[b] | Bad Backbone[c] |
|---|---|---|---|---|---|---|
| ● | ● | ● | ● | 94 ± 42 | 44830 ± 21257 | 30400 ± 10352 |
| ● | ○ | ● | ● | 122 ± 51 | 35637 ± 14064 | 25141 ± 7581 |
| ● | ○ | ○ | ● | 118 ± 62 | 31889 ± 15434 | 22351 ± 7021 |
| ● | ○ | ● | ○ | 166 ± 59 | 59762 ± 18603 | 41853 ± 11133 |
| ● | ○ | ○ | ○ | 155 ± 56 | 51140 ± 17355 | 34331 ± 8936 |
| ○ | ● | ● | ● | 120 ± 28 | 115061 ± 26531 | 72447 ± 12517 |
| ○ | ○ | ● | ● | 128 ± 39 | 62712 ± 11092 | 41722 ± 6856 |

| Crashes[d] | $R_{gyr}$[e] | $R_{NC}$[f] | $R_n$[g] | $C_n$[h] | $C_n/R_n$ | N |
|---|---|---|---|---|---|---|
| 13928 ± 12115 | 39.2 ± 8.3 | 90.4 ± 36.1 | 0.72 ± 0.31 | 4.2 ± 3.1 | 5.5 ± 2.8 | 300 |
| 10012 ± 7109 | 39.4 ± 8.8 | 91.2 ± 36.9 | 0.73 ± 0.33 | 4.3 ± 3.5 | 5.5 ± 2.8 | 300 |
| 9093 ± 9207 | 41.1 ± 9.8 | 97.6 ± 41.6 | 0.80 ± 0.40 | 5.0 ± 4.1 | 5.9 ± 3.0 | 300 |
| 17187 ± 7935 | 47.5 ± 11.0 | 107.3 ± 45.9 | 1.07 ± 0.50 | 6.1 ± 4.8 | 5.3 ± 2.8 | 300 |
| 16175 ± 8830 | 52.0 ± 11.1 | 122.9 ± 46.9 | 1.27 ± 0.55 | 7.8 ± 5.8 | 5.8 ± 2.9 | 250 |
| 42032 ± 15421 | 36.5 ± 8.1 | 84.6 ± 34.7 | 0.63 ± 0.29 | 3.7 ± 2.9 | 5.6 ± 2.9 | 300 |
| 20252 ± 4533 | 39.9 ± 8.8 | 92.2 ± 36.5 | 0.75 ± 0.34 | 4.4 ± 3.3 | 5.5 ± 2.8 | 300 |

[a]From placement of first atom to placement of final atom
[b]One try is an attempt to place a residue, whether successful or not, and is the sum of Bad Backbone errors, Crashes, and successful placements; number of successful placements is usually greater than the length of the protein due to backtracking
[c]Number of tries that failed because no placement of the backbone N and C could be found within the specified backbone error tolerance
[d]Number of tries which failed due to van der Waals collisions
[e]Radius of gyration (Å)
[f]Distance from Cα of first residue to Cα of last residue (Å)
[g]$R_{gyr}^2/rl^2$, where $l = 3.81$Å and r = # residues
[h]$R_{NC}^2/rl^2$, where $l = 3.81$Å and r = # residues Table III - Effects of various simulation conditions on randomly generated structures.

All values given are mean ± s.d. over N structures.

As indicated, either AA-based (●) or completely flat (○) trajectory distributions were used, and the number of attempts before backtracking was either dependent on the shallowness of each trajectory distribution (●), or not (○) (and fixed at 100).

Rotamers were built on-the-fly using the backbone dependent rotamer library (●) or placed statically from a pre-built rotamer dictionary (○) allowing only three possible values for each χ angle.

Either soft (●) or hard (○) atoms collisions were simulated.

400 × 400 trajectory distributions were used in all of the above runs.

| Protein | # residues | Resolution (Å) | Structural class | RMSbb error cutoff | Reconstructed RMSbb error[a] | Crystal structure RMSbb error[a] | Cα RMSD (Å) | C, N RMSD (Å) | Cβ[b] RMSD (Å) | O RMSD (Å) | Cβ, C, N, O RMSD (Å) | R & S Total RMSD (Å) |
|---|---|---|---|---|---|---|---|---|---|---|---|---|
| 1I1M | 154 | 1.88 | α | 13.4° | 7.2° | 2.6° | 0.10 | 0.310 | 0.242 | 0.834 | 0.486 | — |
| 1OMD | 107 | 1.85 | α | 15.5° | 8.3° | 6.0° | 0.09 | 0.249 | 0.274 | 0.735 | 0.411 | — |
| 1SEM | 58 | 2.0 | β | 22.6° | 9.9° | 3.9° | 0.18 | 0.409 | 0.375 | 1.089 | 0.644 | — |
| 3TS1[c] | 211 | 2.7 | α/β | 13.8° | 8.2° | 5.6° | 0.17 | 0.347 | 0.266 | 1.012 | 0.578 | — |
| 4PTI | 58 | 1.5 | α + β | 13.8° | 7.7° | 5.0° | 0.12 | 0.383 | 0.360 | 0.915 | 0.561 | 0.626 |
| 2PCY | 99 | 1.8 | β | 30.8° | 11.2° | 4.7° | 0.59 | 0.707 | 0.404 | 1.342 | 0.861 | 0.725 |
| 2MHR | 118 | 1.7 | α | 22.6° | 9.9° | 5.0° | 0.44 | 0.584 | 0.350 | 1.226 | 0.760 | 0.711 |
| 2LYM | 129 | 2.0 | α + β | 14.5° | 8.3° | 4.5° | 0.24 | 0.407 | 0.275 | 1.204 | 0.681 | 0.765 |
| 1TIM | 247 | 2.5 | α/β | 28.5° | 10.1° | 5.0° | 0.23 | 0.410 | 0.403 | 1.213 | 0.702 | 0.626 |

[a]excludes contributions at Gly residues
[b]estimated by comparing crystal structure to "ideal" look-up table Cβ locations
[c]only the first 211 residues were modelled since certain residues are missing beyond this point
Table IV - Using only the Cα trajectories (i.e. ϕ, θ at each residue) of nine proteins with known folds, the remaining backbone atoms were reconstructed using the method described in the text.
The RMSD co-ordinate deviations of various atom groups between the crystal and reconstructed structures are summarized here, and compare well with Rey and Skolnick's reconstruction technique (4) (last column).
For the last four proteins, high backbone error tolerances were required in order to successfully build the protein with no atomic clashes occuring, most likely due to the occasional incorrect placement of Cβ atoms.

| Distance reported[a] | RMS Distance[b]/Peak (Uniform) (Å) | RMS Distance[b]/Peak (AA-based) (Å) | Experimental[d] RMS Distance (Å) | Experimental[e] Peak at 20° C. (Å) | Experimental[e] Peak at 35° C. (Å) | FWHM[b] (Uniform) (Å) | FWHM[b] (AA-based) (Å) | Experimental FWHM[d] (Å) |
|---|---|---|---|---|---|---|---|---|
| (1-15) | 27.0 | 30.2 | 32 ± 4 | 26.0 ± 6.0 | 24.5 ± 5.0 | 18 | 20 | 25 ± 6 |
|  | 30 | 32 |  |  |  |  |  |  |
| (1-26) | 37.3 | 42.2 | 23 ± 3[c] | 34.8 ± 7.3 | 29.5 ± 7.8 | 33 | 33 | 10 ± 4[c] |
|  | 44 | 45 | 55 ± 15 |  |  |  |  |  |
| (1-41) | 47.1 | 51.9 |  | 39.8 ± 13.4 | 40.0 ± 8.7 |  |  |  |
|  | 46 | 47 |  |  |  |  |  |  |
| (1-46) | 50.1 | 55.2 |  | 39.5–43.6 | 33.3 ± 10.9 |  |  |  |
|  | 45 | 55 |  | ±12.3 –20.0 |  |  |  |  |

[a]The distance from N-terminal α-carbon to Nζ of Lys-15 or Lys-26 is reported, while experimental values are the distance from donor to acceptor probes attached respectively to the N-terminus and ε-amino group on the Lys residue in question
[b]Results over 5000 structures generated with FOLDTRAJ starting with Uniform or AA-based trajectory distributions as indicated. RMS value of distribution is on top, and value at which peak occurs is given below this.
[c]Amir, D. et al, (Proteins 1992, 13:162–173) fit the (1-26) data as two distinct skewed Gaussians, so the RMS and FWHM of each is given
[d]from Amir et al, supra, in 26% (v/v) glycerol, 6M guanadine hydrochloride, reducing conditions, –30° C.
[e]from Gottfried, and Haas (Biochemistry 1992, 31:12353–12362), in 6M guanadine hydrochloride, reducing conditions. Values are given ±1 standard deviation; the authors do not provide an exact value for (1-46) but rather a range, as duplicated above in the table
Table V - Distance distributions in BPTI in randomly generated and experimentally denatured protein.

FULL CITATIONS FOR REFERENCES REFERRED TO IN THE SPECIFICATION

Boris, J. (1986) J. Comput. Phys., 66. 1–20.
Lambrakos, S. G., and Boris, J. P. (1987) J. Comput. Phys., 73, 183–202.
Ambrosiano, J., Greengard, L., and Rokhlin, V. (1988) Computer Physics Communications, 48, 117–125.
Appel, A. W., (1985) SIAM J. Sci. Stat. Comput., 6, 85–103.
Greengard, L., and Rokhlin, V. (1987) J. Comput. Phys., 73, 325–348.
Omohundo. S.M. (1987) Complex Systems, 1, 273–347.
Van Gunsteren, W. V., Berendsen, H. J. C. Colona, F., Perahia, P., Hollenberg, J. P., and Lellouch, P. (1984) J., Comput. Chem., 5, 272–279.
Barnes, J. and Hut, P. (1986) Nature, 324, 466–449.
Karkunkel, H. R. and Eyraud, U. (1989) J. Comput. Chem., 10, 628–634.
Hernquist, L. (1988) Computer Physics Communications, 48, 107–115.
Katzenelson, J. (1989) SIAM J.Sci. Stat. Comput., 10, 787–815.
Lyklema, J. W., (1984) J. Phys A:Math. Gen., 17, L691–L696.
Majid, I., Jan, N., Coniglio, A., and Stanley, H. E. (1984) Phys. Rev. Lett., 52, 1257–1260.
Pietronero. L. (1985) Phys. Rev. Lett., 55, 2025–2027.
Flory, P. J. Statiscial Mechanics of Chain Molecules, Oxford U. Press, 1989.
Knuth, D. E., The Art of Computer Programming—Sorting and searching, Addison-Wesley, 1973.
1. Ngo, J. T. and Marks, J. (1992): Computational complexity of problem in molecular structure prediction. *Protein Eng.*, 5:313–321.
2. Karplus, M. (1997): The Levinthal paradox: yesterday and today. *Fold.Des.*, 2:S69–S75.
3. Onuchic, J. N., Wolynes, P. G., Luthey-Schulten, Z., and Socci, N. D. (1995): Toward an outline of the topology of a realistic protein-folding funnel. *Pro.Natl.Acad.Sci.U.S.A.*, 92:3626–3630.
4. Rey, A. and Skolnick, J. (1992): Efficient Algorithm for the Reconstruction of a Protein Backbone from the a-Carbon Coordinates. *J. Comp.Chem.*, 13:443–456.
5. Holm, L. and Sander, C. (1991): Database algorithm for generating protein backbone and side-chain co-ordinates from a C alpha trace application to model building and detection of co-ordinate errors. *J.Mol.Biol.,* 218:183–194.
6. Correa, P. E. (1990): The building of protein structures from alph-carbon coordinates. *Proteins,* 7:366–377.
7. Dunbrack, R. L. J. and Karplus, M. (1993): Backbone-dependent rotamer library for proteins. Application to side-chain prediction. *J.Mol.Biol.,* 230:543–574.
8. Dunbrack, R. L. Jr. Sidechain placement With a Rotamer Library (SCWRL). (2.0)
9. Hogue, C.W. (1997): Cn3D: a new generation of three-dimensional molecular structure viewer. *Trends.Biochem.Sci.,* 22:314–316.
10. Ostell, J and et al. NCBI Software Development ToolKit. (6.0).
11. Majid, I., Jan, N., Coniglio, A., and Stanley, H. E. (1984): Kinetic Growth Walk: A New Model for Linear Polymers. *Phys.Rev.Lett.,* 52:1257–1260.
12. Flory, P. J. (1989): *Statistical Mechanics of Chain Molecules.* Oxford University Press,
13. Schulz, G. E. and Schirmer, R. H. (1979): *Principles of Protein Structure.* Springer-Verlag, New York.
14. Netzer, W. J. and Hartl, F. U. (1998): Protein folding in the cytosol: chaperonin-dependent and -independent mechanisms. *Trends.Biochem.Sci.,* 23:68–73.
15. Netzer, W. J. and Hartl, F. U. (1997): Recombination of protein domains facilitated by co-translational folding in eukaryotes [see comments]. *Nature,* 388:343–349.
16. Van Gunsteren, W. V., Berendsen, H. J. C., Colonna, F., Perahia, P., Hollenberg, J. P., and Lellouch, P. (1984): On Searching Neighbors in Computer Simulations of Macromolecular Systems. *J.Comp.Chem.,* 5:272–279.
17. Boris, J. (1986): A vectorized "nearest-neighbors" algorithm of order N using a monotonic Lagrangian grid. *J.Comput.Phys.,* 66:1–20.
18. Appel, A. W. (1985): An Efficient Program for Many-Body Simulation. *SIAM J.Sci.Stat.Comput.,* 6:85–103.
19. Omohundro, S. M. (1987): Efficient Algorithms with Neural Network Behavior. *Complex Systems,* 1:273–347.
20. Barnes, J. and Hut, P. (1986): A hierarchical O(N log N) force-calculation algorithm. *Nature,* 324:446–449.
21. Karfunkle, H. R. and Eyraud, V. (1989): An Algorithm for the Representation and Computation of Supermolecular Surfaces and Volumes. *J.Comput.Chem.,* 10:628–634.
22. Hernquist, L. (198): Hierarchical N-body Methods. *Comput.Phys.Comm.,* 48:107–115.
23. Katzenelson, J. (1989): Computational Structure of the N-Body Problem. *SIAM J.Sci.Stat.Comput.,* 10:787–815.
24. Gregoret, L. M. and Cohen, F. E. (1991): Protein folding. Effect of packing density on chain conformation. *J.Mol.Biol.,* 219:109–122.
25. Engh, R. A. and Huber, R. (1991): Accurate Bond and Angle Parameters for X-ray Protein Structure Refinement. *Acta Cryst., A*47:392–400.
26. Wang, Y., Huq, H. I., de la Cruz, X. F., and Lee, B. (1998): A new procedure for constructing peptides into a given Calpha chain. *Fold.Des.,* 3:1–10.
27. Brünger, A. T. X-PLOR. (3.851). 1992. Yale University, New Haven, Conn.
28. Lee, C. and Subbiah, S. (1991): Prediction of protein side-chain conformation by packing optimization. *J.Mol.Biol.,* 217:373–388.
29. Lee, C. (1994): Predicting protein mutant energetics by self-consistent ensemble optimization. *J.Mol.Biol.,* 236:918–939.
30. Hooft, R. W., Vriend, G., Sander, C., and Abola, E. E. (1996): Errors in protein structures. *Nature,* 381:272–272.
31. Cremer, D. and Pople, J. A. (1975): A General Definition of Ring Puckering Coordinates. *J.Amer.Chem.Soc.,* 97:1354–1358.
32. Brant, D. A. and Flory, P. J. (1965): The Configuration of Random Polypeptide Chains. II. Theory. *J.Amer.Chem.Soc.,* 87:2791–2800.
33. Ramachandran, G. N. and Sasisekharan, V. (1968): Conformation of polypeptides and proteins. *Adv.Protein Chem.,* 23:283–438.
34. Lesk, M. (1991): *Protein Architecture.* Oxford University Press, New York.
35. de la Cruz, X. F., Mahoney, M. W., and Lee, B. (1997): Discrete representations of the protein C alpha chain. *Fold.Des.,* 2:223–234.

ABBREVIATIONS

ASN.1—Abstract Syntax Notation 1
BPTI—Bovine Pancreatic Trypsin Inhibitor
CDF—Cumulative Distribution Function
CPU—Central Processing Unit
FRET—Fluorescence Resonance Energy Transfer
FWHM—Full Width at Half-Maximum
MMDB-API—Molecular Modelling DataBase Applications Programming Interface
NCBI—National Center for Biotechnology Information
NMR—Nuclear Magnetic Resonance
PDB—Brookhaven Protein Data Bank
PDF—Probability Distribution Function
RMS—Root Mean Square
RMSD—Root Mean Square Deviation

We claim:

1. A computer-imnplemented method for identifying at least one conformation of a protein of known or unknown structure which comprises the steps of:

(a) providing an amino acid sequence of the protein;

(b) constructing, a backbone structure of α-carbons of the amino acid sequence of the protein by adding and removing carbon atoms through chain elongation and backtracking, which comprises randomly sampling trajectory distributions represerning a statistical sampling from each amino acid of the conformational space it is observed to visit in known proteins, and backtracking using a hierarchical data structure to remove a& atom if it is closer to its neighbor than allowed by van der Waals radii;

(c) positioning β carbons, C, N, and O atoms about the constructed backbone structure of step (b) wherein the atoms are positioned to provide favourable bond lengths and bond angles;

(d) positioning sidechain rotamers including adding hydrogen atoms; and (e) displaying the results of steps (a)–(d); thereby outputting at least one conformation of the protein.

2. A method as claimed in claim 1 wherein in step (c) the conformation of the protein is outputted as an all atom protein structure including hydrogen atoms.

3. A method as claimed in claim 1, wherein the conformation of the protein is constructed in O(NlogN) time, wherein N is the number of residues in the protein and O means the order of the algorithm.

4. A method as claimed in claim 1, wherein in steps (a) to (d) the conformation of the protein is constructed in three dimensional unconstrained space.

5. A method as claimed in claim 1, wherein the trajectory distributions are resolved into α, β, and coil secondary structure components for each amino acid residue.

6. A method as claimed in claim 5 wherein the trajectory distributions are recombined in predicted $\alpha$, $\beta$, and coil secondary structure proportions for each amino acid to form a starling backbone conformation graph.

7. A method as claimed in claim 1, wherein in step (b) a carbon atom is positioned based on a two-dimensional probability distribution function.

8. A method as claimed in claim 1 wherein the conformation of the protein is stored in memory or on a computer storage medium.

9. A method as claimed in claim 1, comprising reiterating steps (a)–(d) an arbitrary number of times before displaying the results of step (e) to provide a plurality of different conformations of the protein.

10. A method as claimed in claim 9, comprising assembling the plurality of different conformations to provide an ensemble of conformations of the protein.

11. A method as claimed in claim 10 wherein the ensemble of conformations of the protein are incorporated in a database.

12. A method as claimed in claim 11 wherein the database comprises about 50,000 to 500,000 different confirmations of the protein.

13. A method as claimed in claim 9 wherein the different conformations of the protein are stored in memory or on a computer storage medium.

\* \* \* \* \*